US010577638B2

(12) United States Patent
Srinivasan et al.

(10) Patent No.: US 10,577,638 B2
(45) Date of Patent: Mar. 3, 2020

(54) SYSTEMS, DEVICES, AND METHODS FOR MICROBIAL DETECTION AND IDENTIFICATION, AND ANTIMICROBIAL SUSCEPTIBILITY TESTING

(71) Applicants: Anand Srinivasan, San Antonio, TX (US); Anand K. Ramasubramanian, San Antonio, TX (US); Jose L. Lopez-Ribot, San Antonio, TX (US); Christopher R. Frei, San Antonio, TX (US)

(72) Inventors: Anand Srinivasan, San Antonio, TX (US); Anand K. Ramasubramanian, San Antonio, TX (US); Jose L. Lopez-Ribot, San Antonio, TX (US); Christopher R. Frei, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 369 days.

(21) Appl. No.: 15/023,568

(22) PCT Filed: Sep. 23, 2014

(86) PCT No.: PCT/US2014/056994
§ 371 (c)(1),
(2) Date: Mar. 21, 2016

(87) PCT Pub. No.: WO2015/042583
PCT Pub. Date: Mar. 26, 2015

(65) Prior Publication Data
US 2016/0215324 A1    Jul. 28, 2016

Related U.S. Application Data

(60) Provisional application No. 61/881,136, filed on Sep. 23, 2013.

(51) Int. Cl.
*C12Q 1/18* (2006.01)
(52) U.S. Cl.
CPC ..................... *C12Q 1/18* (2013.01)
(58) Field of Classification Search
CPC ........................................... C12Q 1/18
USPC ............................................. 506/10
See application file for complete search history.

(56) References Cited

U.S. PATENT DOCUMENTS

| 3,521,624 A * | 7/1970 | Rovee | A61F 13/00042 128/849 |
| 2001/0039032 A1 | 11/2001 | Matsumura | |
| 2007/0184222 A1 | 8/2007 | Delouise et al. | |
| 2008/0213430 A1* | 9/2008 | Segura | A01N 37/46 426/61 |
| 2011/0105360 A1* | 5/2011 | Derda | B01J 19/0046 506/10 |
| 2011/0275114 A1 | 11/2011 | Edberg | |
| 2013/0040854 A1 | 2/2013 | Ramasubramanian et al. | |
| 2013/0053273 A1* | 2/2013 | Juncker | G01N 33/54366 506/9 |
| 2013/0217063 A1 | 8/2013 | Metzger et al. | |
| 2014/0378339 A1* | 12/2014 | Lammertyn | B01L 3/502707 506/9 |

OTHER PUBLICATIONS

Richter SS, MJ. F. 2007. Susceptibility testing instrumentation and computerized expert systems for data analysis and interpretation. Manual of clinical microbiology. American Society for Microbiology: 11 pages.
International Search Report dated Mar. 12, 2015 for application No. PCT/US14/56994; 23 pages. USPTO.
Nightingale J. 1987. Clinical limitations of in vitro testing of microorganism susceptibility. Am J Hosp Pharm 44(1): Abstract only (full text not available).
Barenfanger J, Drake C, Kacich G.; Clinical and financial benefits of rapid bacterial identification and antimicrobial susceptibility testing. Journal of Clinical of Microbioligy. 1999; vol. 37; No. (5): pp. 1415-1418.
Qaseem A, et al. 2012. Appropriate use of screening and diagnostic tests to foster high-value, cost-conscious care. Annals of Internal Medicine; 156(2): 9 pages.
Smith, K., et al., Biofilm formation by Scottish clinical isolates of *Staphylococcus aureus*.J. Med. Microbiol. 2008; pp. 1018-1023.
Srinivasan A, Leung KP, Lopez-Ribot JL, Ramasubramanian AK. 2013. High-throughput nano-biofilm microarray for antifungal drug discovery. mBio 4(4); 11 pages.
Wanger A, Mills K, Nelson PW, Rex JH., 1995; Comparison of Etest and National Committee for Clinical Laboratory Standards broth macrodilution method for antifungal susceptibility testing: enhanced ability to detect amphotericin B-resistant Candida isolates. Antimicrobial Agents Chemotherapy; vol. 39, No. (11):pp. 2520-2522.
Sanchez, C.J.J., et al.,; Biofilm formation by clinical isolates and the implications in chronic infections. BMC Infect. Dis., 2013. vol. 13, No. (47) 12 pages.
Jorgensen JH, JD. T. 2007; Antibacterial susceptibility tests: dilution and disk diffusion methods. Manual of clinical microbiology. American Society for Microbiology;(9th ed.): 7 pages.
O'Toole G, et al.; Biofilm Formation as Microbial Development. Annual Review of Microbiology 54, 2000 (1):pp. 49-79.
Turnidge J, Paterson DL; 2007; Setting and Revising Antibacterial Susceptibility Breakpoints. Clinical Microbiology Reviews; vol. 20; No. (3):pp. 391-408.

(Continued)

*Primary Examiner* — Karla A Dines
(74) *Attorney, Agent, or Firm* — Thomas Horstemeyer, LLP

(57) ABSTRACT

The present disclosure provides for systems, devices, products, and methods for detecting and identifying microbial organisms in a sample as well as testing antimicrobial susceptibility of microbial organisms.

20 Claims, 8 Drawing Sheets

(56) References Cited

OTHER PUBLICATIONS

Dickert H, Machka K, Braveny I. 1981. The uses and limitations of disc diffusion in the antibiotic sensitivity testing of bacteria. Infection 9(1): pp. 18-24.

Church, D., et al.; Burn wound infections. Clinical Microbioligy Reviews; Apr. 2006; 19(2): pp. 403-434.

Mak A, Miller MA, et al.; 2009. Comparison of PCR and culture for screening of vancomycin-resistant enterococci: highly disparate results for vanA and vanB. Journal of Clinical Microbioligy; vol. 47 No. (12):4136-4137.

Wolk DM, et al.; 2009; Multicenter evaluation of the Cepheid Xpert methicillin-resistant *Staphylococcus aureus* (MRSA) test as a rapid screening method for detection of MRSA in nares. Journal of Clinical Microbiol vol. 47(3): pp. 758-764.

\* cited by examiner

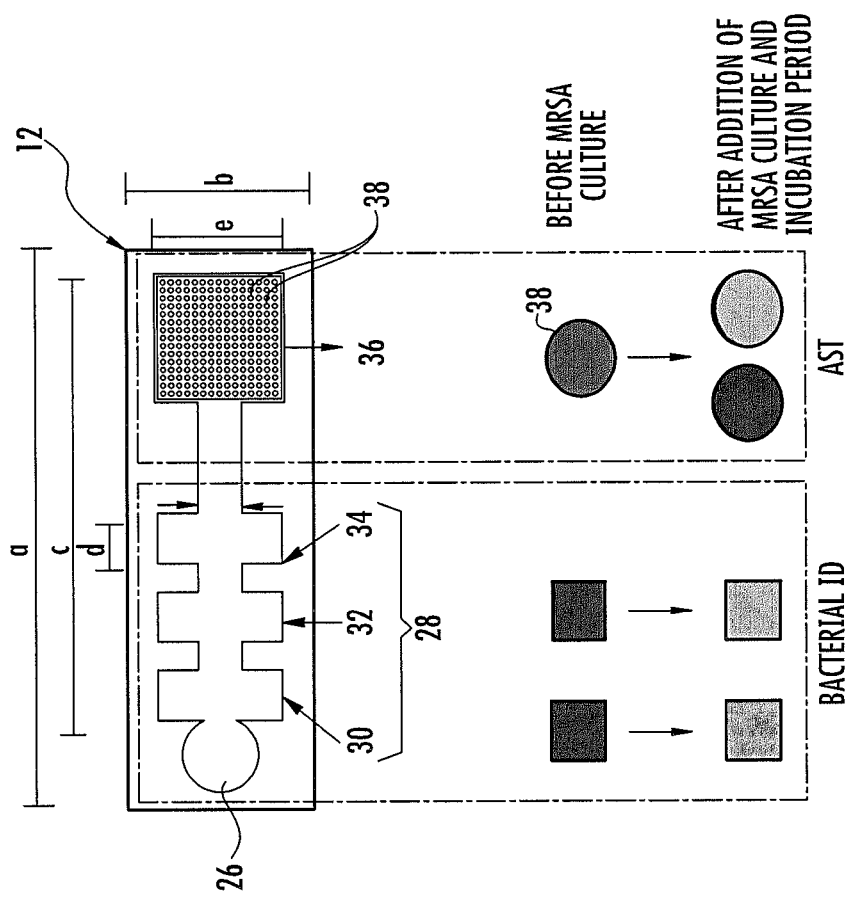
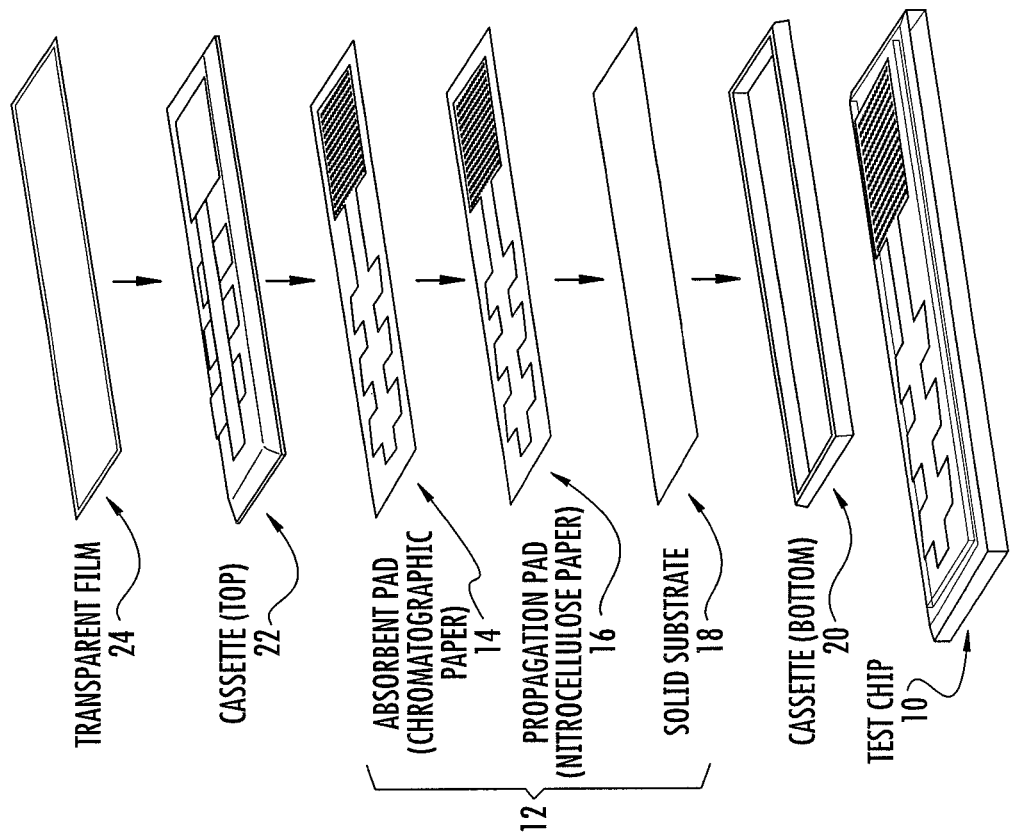
FIG. 2B
FIG. 2A

PERMEATION
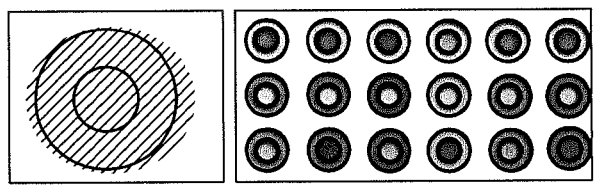
FIG. 3A
CONDUCTION
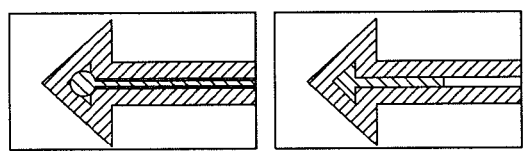
FIG. 3B
HYDROPHOBICITY
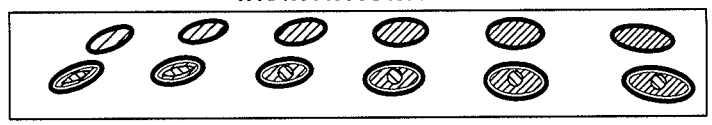
FIG. 3C
AST
- NO-CELL
- LIVE CELLS
- IC50-TREATED
- DEAD CELLS
- PERMEATION
FIG. 3D
INHIBITION
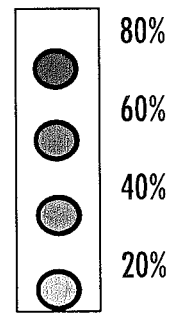
- 80%
- 60%
- 40%
- 20%
FIG. 3E

| INHIBITION OF MICROBIAL COLONIES ON CHIP (%) | | | | | | |
|---|---|---|---|---|---|---|
| CLINICAL ISOLATES | VANCOMYCIN | | DOXYCYCLINE | | CLINDAMYCIN | |
| | MEAN | STD | MEAN | STD | MEAN | STD |
| A32 | 87.37915 | 24.92791 | 81.18298 | 19.78405 | 79.20043 | 13.00166 |
| K2 | 92.70962 | 14.41449 | 80.52382 | 3.995295 | 70.36773 | 10.4368 |
| B2 | 92.92055 | 14.28236 | 82.99789 | 7.043164 | 69.14789 | 9.688162 |
| I27 | 69.37511 | 8.891981 | 76.31833 | 3.090975 | 68.06607 | 4.529541 |
| D1 | 50.1916 | 22.39818 | 72.80717 | 7.478203 | 50.08014 | 9.486547 |
| M2 | 67.55142 | 2.530801 | 68.14467 | 4.522803 | 51.63387 | 5.227364 |
| WT | 51.55563 | 9.943921 | 67.91615 | 11.5795 | 47.80518 | 6.050991 |

SYSTEMS, DEVICES, AND METHODS FOR MICROBIAL DETECTION AND IDENTIFICATION, AND ANTIMICROBIAL SUSCEPTIBILITY TESTING

CROSS-REFERENCE TO RELATED APPLICATIONS

This application is the 35 U.S.C. § 371 national stage of, and claims priority to and the benefit of, PCT application PCT/US2014/056994, filed Sep. 23, 2014, which claims priority to and the benefit of U.S. Provisional Application No. 61/881,136, filed on Sep. 23, 2013, herein incorporated by reference in their entirety.

STATEMENT REGARDING FEDERALLY SPONSORED RESEARCH OR DEVELOPMENT

This invention was made with Government support under grant numbers SC1 HL112629 and R01DE023510 awarded by the National Institutes Health and grant number 13PRE17110093 awarded by the American Heart Association. The Government has certain rights in this invention.

BACKGROUND

For over five decades antimicrobial resistance has presented and remains a major healthcare problem throughout the world, largely due to the indiscriminate use of antibiotics. This liberal usage of antibiotics is partially driven by the clinicians' need to ensure adequate empiric coverage in the face of diagnostic uncertainty and the availability of a small window of opportunity for treatment. Currently, the selection of antimicrobials effective against infectious pathogens is typically performed by first recovering, culturing, and identifying the microorganism(s) from specimens and then testing the susceptibility of these pathogens against various antibiotics over a range of concentrations. Conventional antimicrobial susceptibility tests (AST) are typically performed in suspension assays (e.g., broth microdilution assay) or in agar plate assays (e.g., disk diffusion assay) and take 1 to 3 days. While this process is underway, a wide-ranging treatment regimen is usually adopted based on a number of clinical parameters, local epidemiology, and the suspected causative pathogens. However, it is common for such broad-spectrum treatment to fail, cause adverse effects, or lead to antibiotic resistance and other health issues, such as unacceptable mortality and morbidity, with significant economic and health care ramifications.

It is now established that faster availability of susceptibility data can enable physicians to initiate or switch to an appropriate antimicrobial therapy sooner, thus reducing health care costs due to fewer laboratory tests, invasive procedures, or the length of hospital stay. While there has been some progress in recent years for rapid determination of antibiotic susceptibility, the tests that are currently available are either limited to a few selected organisms, do not reliably predict drug response, or are cost-prohibitive to a significant portion of the population even in developed countries.

SUMMARY

Briefly described, embodiments of the present disclosure provide microbial identification and antimicrobial susceptibility testing (MID-AST) devices, products containing the devices, methods of making and using the devices, and microbial identification and antimicrobial susceptibility testing (MID-AST) systems, and methods of identifying and testing the susceptibility of one or more target microbial organisms in a test sample.

Embodiments of microbial identification and antimicrobial susceptibility testing (MID-AST) devices include: a flat substrate comprising a top surface and one or more layers, a microbial detection and identification (MID) region located in one area of the substrate, and an antimicrobial susceptibility testing (AST) region located in another area of the substrate. In embodiments, the MID region includes one or more spatially distinct identification zones capable of receiving and retaining a portion of a test sample, each identification zone including a medium that selects for growth of one or more target microbial organisms, where detection of growth in an identification zone indicates the presence of the one or more target microbial organisms associated with that zone. In embodiments, the AST region of the device includes at least one array having a plurality of spatially distinct spots capable of receiving and retaining a portion of a test sample, each spot including a growth medium and one or more antimicrobial drugs, where at least one spot has a different drug, combination of drugs, or concentration of drugs than at least one other spot, and where an absence of growth or an amount of growth detected in each spot indicates the susceptibility of the one or more microbial organisms present in the sample to the one or more drugs on that spot.

The present disclosure includes products including the MID-AST device of the present disclosure. In embodiments, the present disclosure includes a bandage including the MID-AST device of the present disclosure.

The present disclosure also includes a microbial identification and antimicrobial susceptibility testing (MID-AST) system. In embodiments, the MID-AST system includes: a rotatable housing having a central sample inlet port for receiving a test sample, a plurality of chambers around the sample inlet port, each chamber adapted for receiving a test cartridge and having an aperture providing fluid communication between the sample inlet port and a cartridge housed within the chamber; one or more test cartridges adapted for placement in a chamber of the rotatable housing, each test cartridge having a plurality of slots and a plurality of channels leading from the aperture of the chamber to the slots and providing fluid communication between the sample inlet port and the slots, each slot adapted for receiving a microbial test chip; and at least two microbial test chips adapted for placement in a slot of a test cartridge, where each test chip includes a flat substrate including one or more layers. In embodiments, at least one test chip is a microbial detection and identification test chip and at least one test chip is an antimicrobial susceptibility test chip.

The present disclosure also provides methods of identifying and testing the susceptibility of one or more target microbial organisms in a test sample. In embodiments, the method includes providing a test sample and contacting the test sample with an MID-AST device of the present disclosure, such that the test sample contacts each of the identification zones and spots of the device. The method also includes incubating the device for a period of time; detecting the presence of a target microbial organism in one or more identification zones, where detecting the presence of the target microbial organism in an identification zone indicates the presence of that microbial organism in the test sample; detecting the growth of a target microbial organism in one or more antimicrobial susceptibility testing spot, where the amount of growth of the target microbial organism on a spot corresponds to the susceptibility of the target microbial organism to the one or more drugs contained on that spot.

In embodiments, the present disclosure also provides methods of making a microbial identification and susceptibility testing device of the present disclosure. In embodiments, the method includes: providing a substrate; modifying a surface of the substrate to provide spatially distinct identification zones in a microbial detection and identification region of the substrate and spatially distinct spots an antimicrobial susceptibility testing region of the substrate; patterning a growth medium composition on each identification zone, where the growth medium composition selects for one or more target microbial organisms and where the growth medium composition is the same or different for each identification zone; patterning a growth medium/drug composition on each spot in the antimicrobial susceptibility testing region of the substrate, where the growth medium/drug composition includes a growth medium and one or more antimicrobial drugs, and where the growth medium/drug composition for at least one spot includes a different drug, combination of drugs, or concentration of drugs than at least one other spot.

Other methods, compositions, plants, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings. Moreover, in the drawings, like reference numerals designate corresponding parts throughout the several views.

FIGS. 2A-2B illustrate different views of an embodiment of a MID-AST device of the present disclosure. FIG. 2A illustrates an exploded view of the device, illustrating various substrate layers and cassette housing. FIG. 2B is a schematic illustration of a top view of an embodiment of a device of FIG. 2A and an illustration of Before/After culturing of test sample showing detectable colormetric changes to identify culture viability/growth.

FIGS. 3A-3E illustrate optimization of printing conditions and directional flow for use of paper substrates for embodiments of the devices of the present disclosure. FIG. 3A illustrates the effect of patterning hydrophobic barriers on paper substrates to prevent permeation of ink and restricting ink samples to a spatially distinct spot. FIG. 3B illustrates a flow pattern of a sample applied to a paper substrate, indicating conduction of a sample in a specific direction. FIG. C illustrates coating hydrophobic polymers providing different orders of hydrophobicity to a paper substrate layer. FIG. 3D illustrates antimicrobial susceptibility of S. aureus cultures against antimicrobial agents, and FIG. 3E illustrates the use of a colormetric viability/growth detection agent (Presto blue) to determine the percent inhibition of the drug contained on the spot as indicated by the extent of viability/growth illustrated by color change.

FIG. 5A is a bar graph illustrating the extent of biofilm formation/microbial growth analyzed at different concentration and combinations of media. FIG. 5B is a series of confocal laser scanning microscopy images of S. aureus cultures/biofilms stained for metabolic activity.

FIG. 6A is a copy of a microarray scanner image of an embodiment of an MID-AST device of the present disclosure with S. aureus cultures exposed to different concentrations of methicillin [MET] on the spots of the device. FIG. 6B is a graph illustrating dose-response antimicrobial susceptibility profile of wild type S. aureus cultures and CA-MRSA cultures against methicillin obtained using the embodiment of the chip illustrated in FIG. 6A.

DESCRIPTION

Figure 1A:
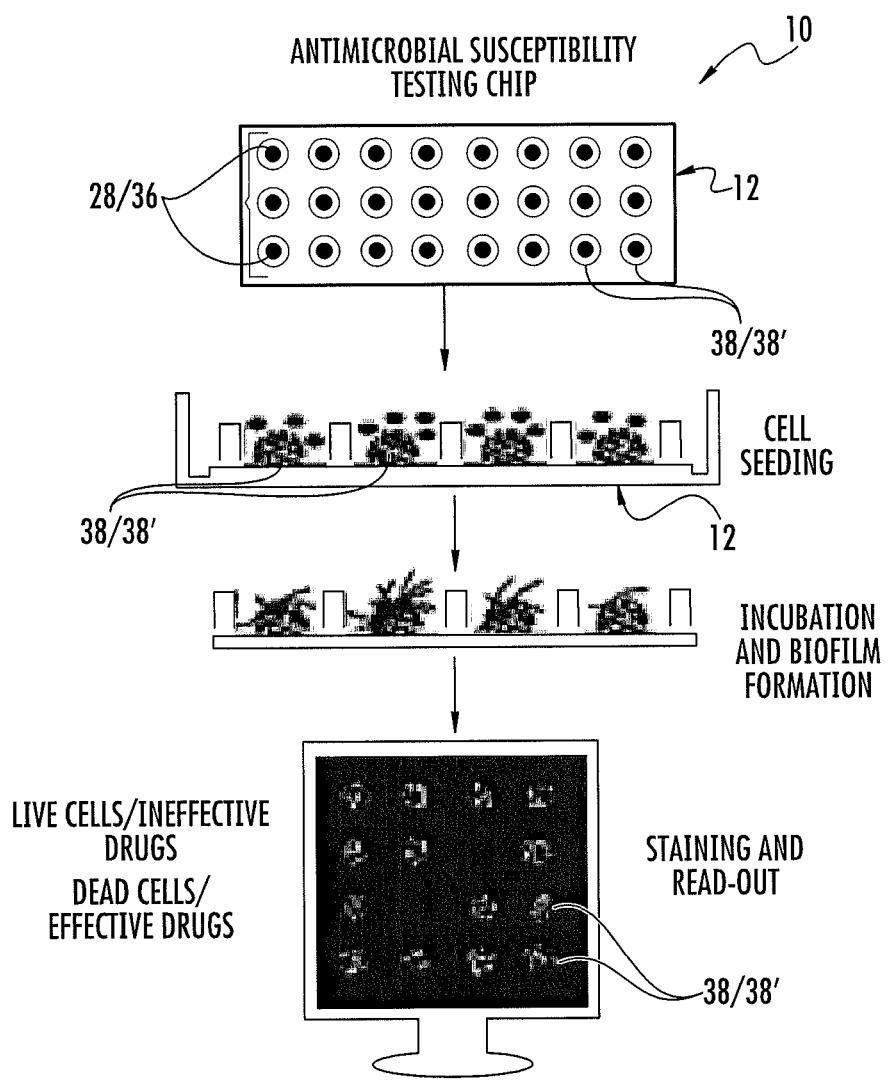
FIG. 1A illustrates an embodiment of a microbial identification and antimicrobial susceptibility testing (MID-AST) device/chip of the present disclosure.
Figure 1B:
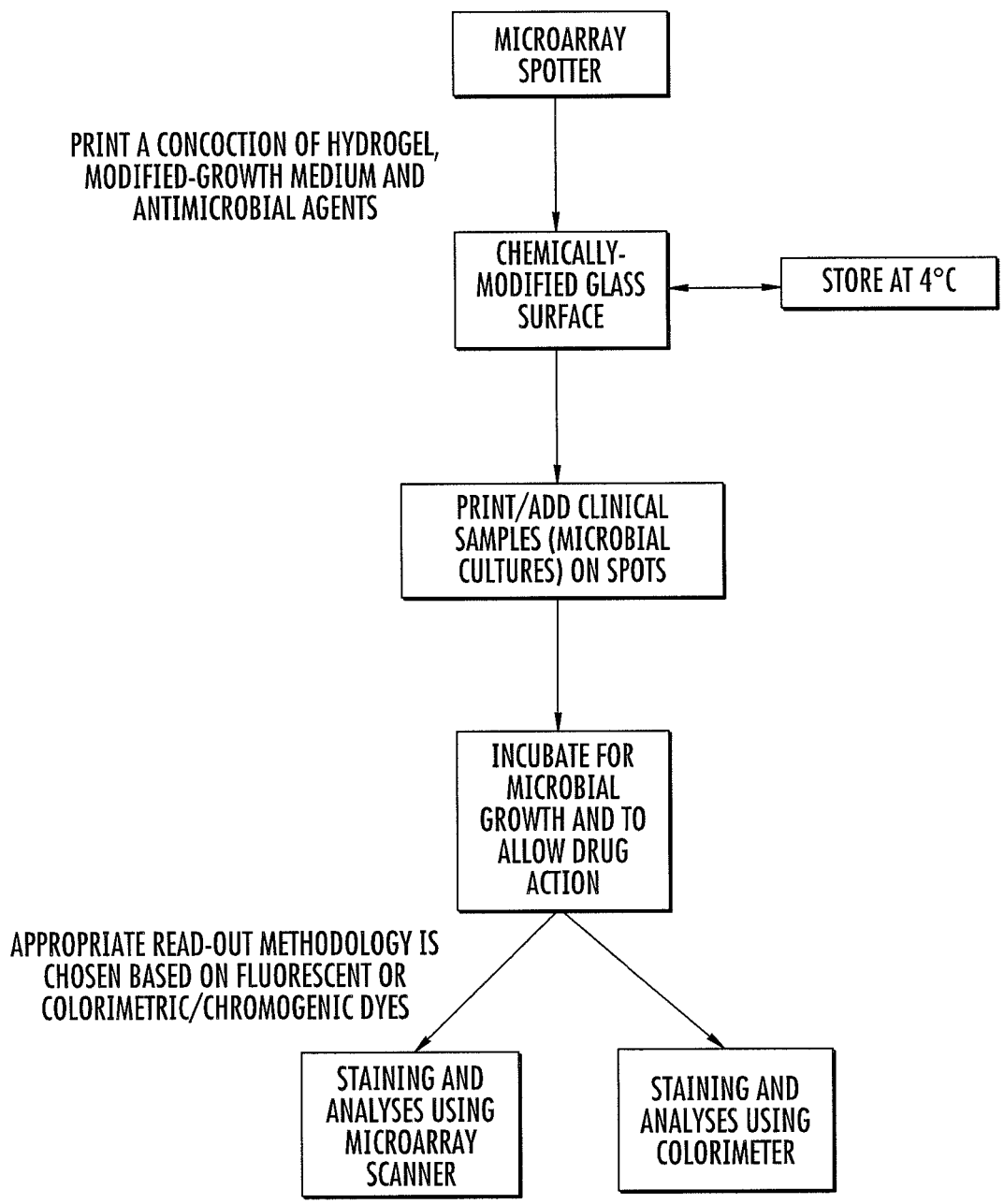
FIG. 1B is a flowchart illustrating an embodiment of a method of the present disclosure of testing for antimicrobial susceptibility in a sample.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Any publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, biochemistry, molecular biology, biology, pharmacology, material science, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent. Throughout this application, the term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and "and/or."

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps. "Consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes any prior art embodiments.

Prior to describing the various embodiments, the following definitions are provided and should be used unless otherwise indicated.

Definitions

In describing the disclosed subject matter, the following terminology will be used in accordance with the definitions set forth below.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides, and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

Use of the term "affinity" can include biological interactions and/or chemical interactions between or among a material (e.g., a compound or bio-molecule (e.g., polypeptide or polynucleotide)) and a cell. The biological interactions can include, but are not limited to, bonding or hybridization among one or more biological functional groups of the compound or cell. The chemical interaction can include, but is not limited to, bonding among one or more functional groups (e.g., organic and/or inorganic functional groups) located on the compound of cells.

An "array" includes any two-dimensional or substantially two-dimensional (as well as a three-dimensional) arrangement of spatially distinct addressable regions ("zones" and/or "spots") including one or more compounds to be tested (e.g., drugs, antibodies, antigens, other peptides, nucleic acids, microbial organisms, etc.) as well as other components, such as media, reporter compounds, and the like. The compounds/materials in each addressable region of the array can be adsorbed, physisorbed, chemisorbed, and/or covalently attached to the arrays, or maintained within the spatially distinct addressable region by a border, such as a hydrophobic border, microchannels, micropatterned borders of hydrophobic materials, and the like. The term "array" encompasses the term "microarray".

A substrate may carry one, two, four or more arrays disposed on a surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than about 20 $cm^2$ or even less than about 10 $cm^2$ (e.g., less than about 5 $cm^2$, including less than about 1 $cm^2$ or less than about 1 mm² (e.g., about 100 µm², or even smaller)). For example, features may have widths (that is, diameter, for a round spot) in the range from about 10 µm to 1.0 cm. Non-round features may have area ranges equivalent to that of circular features with the foregoing width (diameter) ranges.

One or more arrays may form part of a region of a device and/or substrate. It will also be appreciated that throughout the present application, that words such as "top," "upper," and "lower" are used in a relative sense only.

An array, such as those described herein, is "addressable" when it has multiple regions of different moieties (e.g., interactive or binding sites) such that a region at a particular predetermined location (i.e., an "address") on the array can detect a particular outcome for a particular agent and/or interaction. Array features are typically, but need not be, separated by intervening spaces and/or borders.

The term "organism," "subject," or "host" refers to any living entity, including humans, mammals (e.g., cats, dogs, horses, mice, rats, pigs, hogs, cows, and other cattle), birds (e.g., chickens), and other living species that are in need of treatment. In particular, the term "host" includes humans. As used herein, the term "human host" or "human subject" is generally used to refer to human hosts. In the present disclosure the term "host" typically refers to a human host, so when used alone in the present disclosure, the word "host" refers to a human host unless the context clearly indicates the intent to indicate a non-human host.

The term "microorganism" or "microbe" as used herein refers to a small (often, but not always, microscopic) organism that is typically, but not exclusively, single cellular, and includes organisms from the kingdoms bacteria, archaea, protozoa, and fungi. The present disclosure is primarily directed to microorganisms that are pathogenic and capable of causing disease. In embodiments, microorganism includes bacteria and fungi capable of causing disease, particularly disease in humans and other mammals and animals in need of treatment.

The term "sample" can refer to a tissue sample, cell sample, a fluid sample, and the like. A sample may be taken from a host. The tissue sample can include hair (including roots), buccal swabs, blood, saliva, semen, muscle, or from any internal organs. The fluid may be, but is not limited to, urine, blood, ascites, pleural fluid, spinal fluid, semen, wound exudates, sputum, fecal matter, saliva, and the like. The body tissue can include, but is not limited to, skin, muscle, endometrial, uterine, and cervical tissue. While a sample, in the context of the present disclosure, is primarily a biological sample (e.g., from a living host) the sample may also be an environmental sample suspected of contamination by microbes, such as a water sample, food sample, soil sample, and the like. Although a liquid sample and some solid samples may be used as a test sample without modification for testing directly, if a solid sample is to be made into liquid form for testing and/or a liquid sample is to be diluted, a test sample may be made by reconstituting, dissolving, or diluting the sample in a fluid such as water, buffered saline, and the like.

The term "detectable" refers to the ability to perceive or distinguish a signal over a background signal. "Detecting" refers to the act of determining the presence of a target or the occurrence of an event by perceiving a signal that indicates the presence of a target or occurrence of an event, where the signal is capable of being perceived over a background signal.

The term "detectable signal" is a signal derived from non-invasive imaging techniques such as, but not limited to, optical imaging (including with the naked eye) (e.g., colorimetric assays), fluorescent imaging, positron emission tomography (PET), single photon emission computed tomography (SPECT), magnetic resonance imaging (MRI), computer topography (CT), or ultrasound. The detectable signal is detectable and distinguishable from other background signals that may be generated from the host or sample. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background.

DISCUSSION

In accordance with the purpose(s) of the present disclosure, as embodied and broadly described herein, embodiments of the present disclosure relate to systems, methods, and devices for identification of microbial organisms in a test sample and for antimicrobial susceptibility testing. The devices and systems of the present disclosure allow for rapid, point-of-care testing that improves accuracy and timeliness of care. Embodiments of the present disclosure encompass microbial identification and susceptibility testing devices, microbial identification and susceptibility testing systems, methods of making the devices of the present disclosure, methods of identifying and testing the susceptibility of microbial organisms in a test sample, and products including the microbial identification and susceptibility testing devices of the present disclosure.

Antibiotics save lives arguably more than any other class of drugs. However, they are also among the most misused drugs. Possible misuse includes unnecessary prescriptions, inappropriate treatment dose, inappropriate treatment duration, and delayed administration in critically ill patients. The fallout of such misuse includes, but is not limited to, the emergence and spread of antibiotic resistance, toxicity, or side effects, such as *Clostridium difficile* infections, which are very difficult to treat. Further, the delay in the initiation of appropriate antibiotic therapy can be associated with higher patient mortality in certain bacterial infections.

In order to avoid antibiotic misuse and associated negative consequences, it is recommended that the health care providers prescribe the shortest antibiotic course that is likely to be effective, and follow up with a narrow-spectrum therapy as soon as possible based on available microbiology results, including species identification and antimicrobial susceptibility testing data. This approach enables timely termination of antibiotics when the patient lacks evidence of infection, rapid transition to narrow-spectrum therapy, and tailored choice of antimicrobial agent, dose, duration, and route of administration. Such an approach can have a major impact on the care, cost, and outcome of hospitalized and ambulatory patients with infection. For instance, it has been reported that reducing bacterial identification and AST time by 5.2 hours (39.2 vs. 44.4 hours) resulted in a decreased hospital length of stay of 2.0 days at a cost of $1,750 per patient (Barenfanger, J. et al., J Urol. 2011).

Currently, the most popular method for pathogen identification (ID) and antimicrobial susceptibility testing (AST) is a phenotypic assay (i.e., measurement of resistance against various antibiotic doses). Genetic assays are yet to reach widespread and versatile commercial use. An advantage of the phenotypic assays is the highly standardized operation and interpretation of the results as published by the CLSI or EUCAST guidelines (CLSI 2013). However, these methods consume 24-72 hours of critical time because they generally require pure cultures for AST and they need longer incubation times to differentiate between susceptible and resistant strains. The PCR-based techniques, and more recently, MALDI-TOF MS or NMR, can produce quicker results, but are capable of only detecting a few antibiotic resistance genes or markers, respectively, and these metrics may not correlate with phenotypic antibiotic resistance. In addition, these assays do not provide the minimum inhibitory concentration (MIC values) for tested antimicrobials, which can be crucial in guiding clinical decisions. Finally, the cost per assay correlates inversely with the assay duration; hence, rapid methods that require sophisticated instrumentation may be prohibitively expensive for routine clinical testing.

As compared to conventional methods for microbial detection and susceptibility testing, the devices, systems and methods of the present disclosure operate with smaller sample volumes, have a shorter detection time, provide improved or comparable sensitivity, are less expensive, and may be used on-site at a clinical microbiology lab with minimal training. Furthermore, embodiments of the devices and systems of the present disclosure are culture independent; in other words, the detection and AST are integrated such that the devices are designed to work without the need to separately culture the sample on selective growth plates.

Microbial Identification and Antimicrobial Susceptibility Testing Device

The present disclosure provides microbial identification and antimicrobial susceptibility testing (MID-AST) devices. Embodiments of these devices are designed to provide rapid, on-sight identification (ID) of microbial organisms (e.g., bacteria, fungi, etc.) present in a test sample (e.g., from a patient) and simultaneous antimicrobial susceptibility testing (AST) to determine the susceptibility of any microbes present in the sample to available antimicrobial drugs (including in various combinations and concentrations).

The MID-AST devices of the present disclosure may be embodied in different formats, examples of which are illustrated in FIG. 1A and FIGS. 2A and 2B, but share certain features to provide the ability to perform the desired functions of MID and AST of one or multiple microbial organisms from a test sample in a relatively rapid time-frame on a relatively small-scale device. Some embodiments described here will use materials and techniques more appropriate for a full laboratory setting and, while others are adapted for use in a clinical setting. Some variations of the MID-AST device will be discussed in greater detail below. The following general descriptions will refer to certain features, identified by reference numbers, illustrated in FIG. 1A and FIGS. 2A and 2B below, with respect to the illustrated embodiments. These references are illustrative and not meant to restrict the scope of the device to the specific embodiments illustrated.

In embodiments, a microbial identification and susceptibility testing device (10) of the present disclosure includes a flat substrate (12) comprising a top surface and one or more layers. The device further includes a microbe detection and identification (MID) region (28) located in one area of the substrate and an antimicrobial susceptibility testing (AST) region (36) located in another area of the substrate. While FIGS. 2A and 2B illustrate a distinct MID region and AST region, in some embodiments of MID-AST devices of the present disclosure, such as illustrated in FIG. 1A, these two regions are not as distinct and may be provided by array spots (38, in FIG. 1A) in an area of the substrate, with some spots (38') configured for detection and identification functions and other spots (38) configured for AST functions, as described in more detail below.

The MD &ID region includes one or more spatially distinct identification zones (30, 32, 34, FIG. 2B, but which may be provided by individual spots, such as in the device of FIG. 1A) capable of receiving and retaining a portion of a test sample. Each ID zone includes a medium that selects for growth of one or more target microbial organisms, such that detection of growth in an ID zone indicates the presence of the one or more target microbial organisms associated with that zone.

The AST region (36), located in another area of the substrate includes at least one array including a plurality of spatially distinct spots (38) capable of receiving and retaining a portion of a test sample. Each spot includes a growth medium and one or more antimicrobial drugs. At least one spot includes a different drug, combination of drugs, or concentration of drugs than at least one other spot. In embodiments, each spot in the AST region may contain a different drug, combination of drugs, or concentration of drugs than every other spot, but in other embodiments, at least some of the spots may contain the same drugs in the same concentrations. Duplicate spots may be used for confirmation or for testing susceptibility of a different microbial organism to the same drug/combination/concentration, in which case while the drug may be the same as another spot, the growth medium may be different to select for growth of a different microbial organism. An absence of growth (as determined by a viability or growth detection agent, described below) or the amount of growth (as determined by a relative signal from a growth detection agent, as described below) detected in each spot indicates the susceptibility of the one or more microbial organisms present in the sample to the one or more drugs on that spot. In addition, the AST region provides the ability to deterring the minimum inhibitory concentration (MIC) value of an antimicrobial drug with respect to a target microbial organism. In embodiments, the AST region includes a plurality of spots including the same antimicrobial drug (or combination or drugs), with each spot comprising a different concentration of the drug. Analysis of the amount of growth detected in each spot provides a MIC value with of the antimicrobial drug with respect to a target microbial organism in the test sample.

In embodiments of the MID-AST device of the present disclosure, the microbe detection and identification region (28) includes at least one selective identification zone (32/34) and at least one permissive identification zone (30). The permissive identification zone includes a non-selective growth medium that allows non-selective growth of multiple micro-organisms, and the selective identification zone includes a selective growth medium that selects for growth of one or more specific target microbial organisms. For example, the non-selective medium in the permissive identification zone can be, but is not limited to, blood agar, which allows growth of multiple microorganisms. In embodiments, the non-selective medium is a media, such as organism selective agar or agar loaded with specific antimicrobials, that has been optimized for the growth of polymicrobial species including gram positive and gram negative bacteria, and fungi.

In embodiments where one or more target microorganisms is a bacterial organism the selective medium in the one or more selective ID zones is optimized to select for one or more specific types of microorganism (e.g., a specific genus or species of bacteria, or fungi, or both). In an embodiment, at least one target microbial organism is *Staphylococcus aureus* and the selective medium in at least one selective ID zone is optimized to select for *S. aureus*. In an embodiment the selective media is made of a combination of YPD or BHI, human serum (e.g., 10%), sodium chloride (e.g., 7.5%), lipovitellin, and mannitol for selectively growing *S. aureus*. In embodiments, at least one target microbe is an antibiotic-resistant bacterium, and the selective media for at least one selective ID zone is includes an antibiotic to select for the antibiotic-resistant bacterium. In an example of such an embodiment where a target microbial organism is methicillin-resistant *S. aureus* (MRSA), the selective media is a MRSA selection media including methicillin, nafcillin, or both. In embodiments, the device is configured such that at least one identification zone is an *S. aureus* selective identification zone having an *S. aureus* selection media and at least one other identification zone is a MRSA selective identification zone having a MRSA selection media including methicillin, nafcillin, or both.

In embodiments, the selection media may include antigens and/or antibodies specific for a target microorganism or group of microorganisms in a sample. In embodiments, such as where a target microorganism includes specific bacteria of fungi, the selection media may include antigens and/or antibodies specific for the target bacterial or fungal organisms in the sample. In some embodiments, the antigen or antibodies may be tagged to fluorophores, quantum dots, enzymes for chromogenic substrates, or other reporter molecule capable of producing a detectable signal.

In order to detect the viability or growth of microorganisms in the ID zones and the AST spots, a viability and/or growth detection agent can be used to indicate the presence of or growth of a microorganism in the zone or spot. The growth/detection agent can be a compound capable of producing a detectable signal in the presence of a viable microorganism. Suitable viability/growth detection agents can produce a detectable signal that can be detected by visual inspection (e.g. by the naked eye) or with the assistance of an imaging device. In embodiments, viability/growth detection agents for use with/in the devices of the present disclosure include, but are not limited to, fluorescent molecules/dyes, colorimetric dyes, and chromogenic dyes. In embodiments, the detectable signal is based on a chromogenic signal detected by a chromogenic read out based on the change in pH due to the growth of the organism(s). In embodiments, pH can be measured using standard pH-sensitive reagents such as phenolphthalein, bromothymol blue or methylene red. Such read-outs are particularly useful for clinical or OTC-type assay systems because the assay can be read qualitatively by naked eye or as picture using, e.g., a cell phone. In some embodiments, the viability detection agent is a viability dye capable of indicating viability by producing a chromogenic read-out based on the viability of the organism(s) stained using a viability dye such as Alamar blue or Presto blue. Such embodiments may be useful either for OTC-type assays or more sophisticated laboratory assays. In some aspects detection of viability and/or growth is based on a fluorogenic read-out corresponding to the viability/growth of the organism(s) stained using a viability dye such as, but not limited to, BacLight, FUN1, and the like. The fluorogenic signals/images are read using equipment such as a microarray scanner and analyzed. This assay is highly quantitative and is used in a laboratory setting. While some such viability/growth detection agents indicate the presence of a viable microorganism by producing a signal, they may also detect a level of growth (negatively corresponding to a level of susceptibility to a drug contained on a spot) based on the strength or quality of the signal (e.g., a brighter fluorescence indicates more growth; or a darker color or different color indicates more growth, whereas a fainter fluorescent or fainter/different color indicates less growth, thereby indicating susceptibility).

In embodiments, the viability/growth detection agent can be contacted with the device (e.g., spotted on the device in the ID zones and/or AST zones) after addition of a test sample (before or after incubation of the test sample on the device), e.g., at the end of the assay. In other embodiments each identification zone and each spot include a viability detection agent, a growth detection agent. In such embodiments, the viability/growth detection agent can be spotted on with the drug/media mixture.

In embodiments of the MID-AST device of the present disclosure at least one antimicrobial drug in one or more spots in the AST region is an antibiotic. In embodiments, at least one antimicrobial drug in one or more spots in the AST region is an antifungal drug. In embodiments the antifungal drug includes, but is not limited to, a polyene antifungal drug, an azole antifungal drug, an echinocandin antifungal drug, and the like, or combinations of these. In embodiments where the MID-AST device is to be used to detect and test target bacteria and fungi, some spots include one or more antibiotics and other spots includes one or more antifungal drugs and some spots may include both.

Where at least one target organism is a bacterial organism, such as, but not limited to, one or more *staphylococcus* bacteria, at least some of the spots include an antibiotic including, but not limited to, oxacillin, vancomycin, clindamycin, ciprofloxacin, doxycycline, erythromycin, tetracycline, gentamycin and trimethoprim-sulfamethoxazole, or combinations of one or more of these antibiotics. In embodiments, the antibiotics are present in different concentrations and/or different combinations in different spots.

While in some embodiments, such as depicted in FIG. 1A, the test sample can be spotted on the device in the spots for the ID zones and the AST spots (e.g., by a microarrayer, printer, pipettor, etc.), in other embodiments, such as illustrated in FIG. 2A, the MID-AST device includes a sample inlet (26) for receiving a test sample on the substrate. In embodiments, the substrate is adapted to direct flow of the sample from the inlet to the identification zones (30, 32, 34) of the MD & ID region (28) and the spots (38) of the AST region (36).

In some embodiments of the MID-AST device of the present disclosure, in order to provide additional structural support/isolation to the ID zones and AST spots in the device, the zones and spots also include a matrix material. In embodiments, the matrix material is admixed with the growth medium/drug composition prior to spotting on the substrate. In embodiments the matrix material is a gel material, such as a solgel or hydrogel that provides additional structural support/stability to the zones/spots. The matrix material provides support for the selective (or permissive) media in the identification zones and for the growth medium/drug combinations in the spots of the AST region. In embodiments, the matrix material at least partially supports or encapsulates the selective media in the identification zones and the growth medium and drug combinations in the spots in the susceptibility testing region. In embodiments, the matrix material/medium/drug combination is spotted onto the substrate and forms self contained "islands" on the substrate, such as illustrated in the spots 38/38' in FIG. 1A. As used in the present disclosure, encapsulation indicates the growth medium/drug compositions are at least partially contained within the volume of a matrix material. Encapsulation within the volume of a matrix or adherence to the surface of the matrix can help to maintain the activity of the medium and drugs, and microbial cells (after addition). Furthermore, the volume of a matrix can contain more medium/drug/cells than can be attached to a surface area equal to the footprint of a matrix spot. Depending on the matrix material, the other materials (growth/selection media, drugs, etc.) may be physically encapsulated within the matrix, and/or can be adhered (such as by being covalently attached by a chemical bond) or tethered to the matrix material. In embodiments, the matrix material is at least semi-permeable to allow microbial cells/organisms present in a test sample to permeate the matrix material to contact the growth medium/drug compositions within the matrix material. The matrix material can be spotted on the substrate of the MID-AST device of the present disclosure by various methods, such as spotting with a robotic microarray spotter, manual pipetting, and the like.

When a matrix material is included in the zones/spots, in some embodiments, the matrix material can include materials such as, solgels, or a natural or synthetic hydrogels. Exemplary solgels can be substituted or unsubstituted and can include, but are not limited to tetramethoxyorthosilicate, a methyl-trimethoxyorthosilicate, a tetraalkoxyorthosilicate, and a trialkoxyorthosilicate. Hydrogels can include substituted and unsubstituted, synthetic and natural hydrogels and can include inorganic polymers, organic polymers (PEG, PLGA, PGA, polyacrylamide, agarose, PVA, gelatin-comethacrylate, etc.) and/or natural polymers (collagen, alginate, matrigel, chitosan). Hydrogels include polysaccharide gels, such as, but not limited to, an alginate, a dextran, a starch, a cellulose, a carrageenan, a poly(hyaluronic acid), a heparin, a guar, or an inulin. Other polymers include a polyvinylene, a poly (vinyl acetate), a poly(ethyl vinyl ether, a polyacrylate such as a polymethyl methacrylate, a polystyrene, a polyvinyl silicate, a polyurethane, a polyalkanoate, a poly(lactic acid), a poly(3-hydroxybutyrate), and substituted variations thereof. In embodiments, the matrix material is selected from the group of solgels and hydrogels consisting of: a tetramethoxyorthosilicate, a methyl-trimethoxyorthosilicate, a tetraalkoxyorthosilicate, a trialkoxyorthosilicate, a polyacrylamide, a polyacrylate, a sugar-substituted polyacrylate, polyethylene glycol (PEG), a polyvinyl alcohol, agarose, collagen, matrigel, alginate, chitosan, and other polysaccharide gels. In embodiments, the matrix material includes collagen and/or alginate. The concentration of these hydrogels can range from 0.01% to 10%; depending upon the choice and combinations of the hydrogels. Non-limiting examples include: Collagen at 0.5%, alginate at 1% and matrigel at 0.3%

Various substrates can be used for the MID-AST devices of the present disclosure. In embodiments the substrate can be a single, solid substrate and can be further modified by addition of various coatings/layers. In other embodiments the substrate includes one or more layers of flexible, absorbent and/or permeable materials, such as for applications directly on wounds as a dressing/bandage. In other embodiments, the substrate may be a rigid material. In embodiments, the substrate is a solid substrate, such as, but not limited to, glass, quartz (e.g., as in a microscope slide), a metal substrate, a silicon substrate (e.g., as in a semiconductor wafer), a polymeric material (e.g., PDMS, PMMA, PTFE, polycarbonate, etc., and combinations of these materials). In embodiments, the substrate is a solid support that is flat, thin, and solid, such as a glass/quartz microscope slide or a silicon wafer. The substrate may be in the shape of disks, strips, or slides.

In some embodiments, particularly in embodiments where the substrate is a solid substrate, such as a glass/quartz slide or silicon wafer, the substrate is further treated with a support coating/layer of material to improve adhesion of a matrix material/medium/drug composition. In embodiments the support layer includes one or more hydrophobic or hydrophilic materials. In some embodiments, a hydrophobic polymer may be applied to the substrate (e.g., glass/quartz slide, silicon wafer, polymeric slide, etc.). For purposes of the present disclosure a polymer is considered to be hydrophobic or water-insoluble if it is "sparingly soluble" or "practically insoluble" or "insoluble" as defined by USP29 I NF 24. Examples of hydrophobic polymers include, but are not limited to, acrylic acid-based polymers, methacrylic acid based polymers, and acrylic acid-methacrylic acid based copolymers, and polyolefins (e.g., polystyrene) and modified polyolefins (e.g., polystyrene-co-maleic anhydride (PSMA)), and wax. Other materials that can be used in a support coating/layer include siloxane adhesive materials. For example, amino-siloxanes (e.g., 3-aminopropyltriethoxysilane) may be used to improve adhesion of materials forming the zones/spots to the slide. In one embodiment, a combination of a siloxane adhesive material and a hydrophobic polymer is used to treat a substrate prior to spotting the substrate with growth medium/drugs/matrix material compositions. In embodiments, other materials may be used to coat a substrate, and include, but are not limited to, proteins (e.g., collagen, poly-L-lysine), carbohydrates (hyaluronic acid), peptide tethers, and exopolysaccharide components of a biofilm matrix.

In embodiments of the DIM-AST device of the present disclosure, the support layer is a material selected from, but not limited to, polystyrene-co-maleic anhydride, poly-methyl-methacrylate, polystyrene, poly-vinyl chloride, co-polymers of styrene, olefins, acrylics, amides, imides, dienes, esters and ethers, silicone. In some embodiments, the substrate is a microscope glass slide modified with hydrophobic (e.g., polystyrene or PMMA-based) or hydrophilic (e.g., poly-L-lysine, poly acrylic-based, polyethyleneglycol, polyvinylalcohol) polymers. In some embodiments, the substrate is a glass slide and includes a support layer of poly(styrene-co-maleic anhydride) (PSMA).

In some embodiments, the substrate may also be modified with a "tie-layer" which may be used in conjunction with a support layer (e.g., on top of the support layer) or alone. In embodiments, the tie-layer is spotted on top of the substrate surface and/or on top of the support layer in a pattern corresponding to the pattern of the MID zones and AST spots. If the tie-layer includes a pattern, such as spots, it is a non-contiguous layer. In embodiments, the tie-layer is a mixture of poly-l-lysine and barium chloride or calcium chloride, poly-l-lysine and polyethyleneglycol. In a particular embodiment, the tie-layer is made of 30 nl spots of a mixture of poly-l-lysine and barium chloride and can be applied by spotting with a robotic microarrayer or by manual pipetting, or other appropriate methods.

In some embodiments of the MID-AST device of the present disclosure, the substrate includes one or more layers each layer is made of or more materials selected from, but not limited to: alumina, zirconia, a calcium phosphate, glass, bioactive glass, a glass derivative, porcelain, carbon, paper, gauze, silicone, nitrocellulose, polydimethylsiloxane, plastics (such as, but not limited to, polycarbonate, polymethyl methacrylate, polystyrene, polyvinylchloride, and their copolymers), a stainless steel, and an alloy of chromium, nickel, titanium, gold, silver, or platinum. In embodiments, a layered substrate is made of flexible and/or disposable materials for use in a disposable cassette (such as for the MID-AST systems described below) or for inclusion/integration into products such as bandages/wound dressings. In such embodiments, the substrate can be made from layers of materials such as paper, nitrocellulose pads, gauze, and the like.

As mentioned above, in some embodiments of the MID-AST device of the present disclosure, the substrate is made of at least two layers, such as the embodiment illustrated in FIG. 2A. In embodiments, one layer is a propagation layer (16) adapted to conduct the test sample from a sample inlet (26) to the different regions of the device, and one layer is an absorbent layer (14) disposed adjacent to the propagation layer. In embodiments, the absorbent layer is the top substrate layer and includes the patterned zones/spots of media/drug compositions (with or with out matrix material).

In embodiments the propagation layer is a propagation pad made of a hydrophobic material capable of conducting fluids (e.g., a test sample) to various regions of the substrate. In embodiments, the propagation layer includes materials selected from the group including, but not limited to, papers such as, but not limited to filter papers and chromatographic papers, nitrocellulose membranes, Hi-Flow Plus membranes, Sure Wick Pads, poly(3,4-ethylenedioxythiophene), cellulose-co-carbon fibers, cellulose-co-graphene and other cellulose-copolymers, In some embodiments, the propagation layer is a pad of nitrocellulose paper.

In some embodiments the propagation layer is micropatterned to facilitate the flow/conduction of fluids on/within the substrate. In embodiments, the propagation layer includes micropatterns made with a hydrophobic material, such as, but not limited to paraffin, wax, transparent tape, poly-methyl-methacrylate, polystyrene, poly-vinyl chloride, polydimethylsiloxane, co-polymers of styrene, olefins, acrylics, amides, imides, dienes, esters and ethers, silicone.

The micropatterns can be in various configurations, for instance, microchannels to direct the flow of the test sample, and microborders corresponding to various spatially distinct regions, zones, or spots on the substrate where the microborders provide a hydrophobic barrier around each zone and spot such that they are spatially distinct. For instance (as illustrated in FIG. 2A) the propagation layer (and/or other layers) may include microborders delineating areas such as the sample inlet (26), the ID zones (30, 32, 34) and the spots (38) of the AST region (36). Examples of micropatterns and microchannels for conduction and microborders for delineation and permeation control are illustrated in FIGS. 3A and 3B. These microchannels and borders can be created by techniques including, but not limited to: i) laser etching or engraving the surface of the substrate to create the desired pattern in nano-to-micro scale volumes, or ii) microspotting, coating or printing hydrophobic polymers (such as those mentioned above) on the surface of the substrate.

In embodiments of the MID-AST device of the present disclosure including an absorbent layer as part of the substrate, the absorbent layer can be in the form of an absorbent pad and can include materials such as chromatographic paper, other absorbent papers, gauze, etc. In embodiments, the absorbent layer includes materials selected from the group including, but not limited to, filter papers, chromatographic papers, nitrocellulose membranes, Hi-Flow Plus membranes, Sure Wick Pads, cellulose-co-carbon fibers, cellulose-co-graphene and other cellulose-copolymers membranes. The absorbent layer can also include micropatterns corresponding to the identification zones and the distinct spots of the susceptibility testing region, as described above with respect to the propagation layer. In embodiments, a substrate of the device may not include a propagation layer and may only include an absorbent layer, or a single layer may perform both absorbance and propagation functions. In embodiments, the absorbent layer in a multi-layered substrate is the top layer, on which the growth/selective media (with or without matrix material) for the identification zones and the growth medium and drug combinations (with or without matrix material) for the spots in the susceptibility testing region are spotted. In embodiments, these materials are patterned on the absorbent substrate layer with a microarray spotter or printer. Using paper as the absorbent layer facilitates quick and easy printing of patterns/spots.

In embodiments of the MID-AST devices of the disclosure, micropatterning of channels, borders, regions, spots, etc. can be done with various materials of a variety of substrate materials. For instance, the materials and micropatterns described above with respect to the propagation pad and absorbent pad can also be used on a solid substrate, such as, but not limited to, a glass or silicon slide. In some embodiments, micropatterning can be used to create nanowells on a substrate for the different addressable regions (e.g., zones/spots, etc.) or microchannels for directing the flow of a liquid to various regions on the substrate. Thus, even if not specifically described herein, it is understood that micropatterning techniques and other features described in conjunction with a specific substrate or embodiment may also be applied to other substrates and embodiments.

In some embodiments of the MID-AST devices of the present disclosure, particularly embodiments including a substrate that includes layers of a flexible or absorbent material, such as paper, the substrate can also include a bottom layer under the propagation layer, absorbent layer, and/or other layers, where the bottom layer is a solid substrate. This bottom layer can provide structural integrity to the substrate and device, and can also provide a liquid impervious barrier. In an embodiment, such as illustrated in FIG. 2A, the substrate includes a top absorbent layer (14) and middle propagation layer (16) and a bottom solid layer (18). In embodiments, the solid layer can include any of the materials described above for solid substrates, such as, but not limited to, glass, quartz (e.g., as in a microscope slide), a metal substrate, a silicon substrate (e.g., as in a semiconductor wafer), a polymeric material (e.g., PDMS, PMMA, PTFE, polystyrene, polycarbonate, etc.) and combinations of these materials.

In embodiments, the MID-AST device of the present disclosure also includes a cassette adapted to house the substrate. The cassette can include a bottom tray and, optionally, a top cover. In embodiments, the bottom tray is adapted to receive the single or multi-layered substrate. In embodiments, the cassette also includes a top cover, and the top cover is configured to include apertures/windows to allow a user to view the top of the substrate in order to obtain a read out of the results of the microbial identification and/or antimicrobial susceptibility assays. In embodiments, the top cover includes at least one aperture to accommodate the sample inlet. The top cover can also include windows (open or covered) and/or apertures corresponding to the location of the identification region and the AST region for viewing assay results. If included in the device, the cassette can be made of materials such as glass, plastic, and/or polycarbonate.

In embodiments including a cassette, the cassette can also include a humidifying agent to maintain adequate moisture within the device. In embodiments, the humidifying agent can be, but is not limited to, glycerol, petroleum jelly, silicone gels, and halides of sodium and potassium In embodiments, the MID-AST device includes a glycerin coating/lining within the cassette to maintain moisture.

In some embodiments of the device of the present disclosure, the bottom tray of the cassette and/or the bottom solid substrate layer may also include microchannels and/or microborders connecting and/or delineating the various regions of the device. Such microchannels and microborders may be patterned on the cassette tray or solid substrate layer, or they may be molded onto the tray or substrate layer by methods known in the art.

In embodiments of the MID-AST device, the device may also include a transparent film on the top of the device (e.g., on top of the top surface of the substrate or the cassette top, if present). The transparent film can provide protection of the device from contamination while still allowing visibility to the MID zones and AST region of the substrate. The transparent film can be made of materials including, but not limited to: tape, glass, cover slips, magnifying lenses, transparent polymers such as polycarbonate, and the like.

In general, the MID-AST devices of the present disclosure can be made in a variety of sizes and dimensions. In general, the devices and substrates of the devices are small enough for practical use and to overcome disadvantages with larger devices, such as using agar plate assays and standard well plates. Typically, the volume of the spots on the device will be in the micro- and/or nano-liter range.

For purposes of illustration, some example dimensions are described here with reference to FIG. 2B. In embodiments, the MID-AST device (10) and/or substrate (12) has a length (a) of about 2.5 cm to about 15 cm (e.g., about 7.5 cm) and a width (b) of about 0.1 cm to about 5 cm (e.g., about 2.5 cm). In embodiments, the MID zones (e.g., zones 30-32, 34) have a dimension (d) of about 0.1 cm to about 2 cm (e.g., about 0.5 cm). The AST region (36) can have a dimension (e) of about 0.2 cm to about 5 cm (e.g., about 2.0 cm). The length from the inlet to the end of the addressable regions (c) can be about 1 cm to about 14 cm (e.g., about 5 cm). In embodiments, microchannels patterned on the device can have a diameter of about 10 µm to about 200 µm (e.g., about 0.8 cm).

In embodiments each spots of the substrate can have a volume from about 0.1 nl to about 1 µm. In embodiments, the device can include from about 100 to about 2000 spots, although more or less is also possible. In embodiments, the MID zones can also be spots, such as in an embodiment illustrated in FIG. 1A, or the image shown in FIG. 6A, where the microbial ID region would correspond to the area of the array where the spots did not contain drug, and thus allowed selective growth of the microorganism. In other embodiments, such as shown in FIG. 2A/2B, the MID zones are larger than the spots in the AST region. As discussed above, in some embodiments, instead of self-contained spots, nanowells can be patterned onto a substrate to provide the spots. In some such embodiments, the nanowells can have a volume of about 1 to about 500 nL.

The MID-AST devices of the present disclosure are designed to provide results within about 3 to about 24 hours, depending on the type of organisms being detected. Typical assays to be performed by the MID-AST devices of the present disclosure will have a duration on the present devices of about to about 24 hours. For instance a MID-AST device designed for identification and susceptibility testing for a single bacterial organism in a sample may have a duration of about 4 to about 12 hours, whereas a MID-AST device designed for identification and testing of a single fungal organism may have a duration of about 18 to about 24 hours. Polymicrobial (multiple strains and/or species) MID-AST devices may have a duration of about 12-24 hours.

Embodiments of the present disclosure also include products that include the MID-AST devices of the present disclosure. In some embodiments, the MID-AST device is a point-of care device used for rapid detection of microorganisms, such as bacteria, fungi, and is used to identify the organisms in a sample and to screen samples and clinical isolates against a panel of drugs. In yet other embodiments the MID-AST device is a laboratory screening toll for identifying the susceptibility of either single or multiple microorganisms and to screen for emergence of new drug-resistant strains of a microorganism.

In some embodiments, the MID-AST device can be used as an over-the-counter detection product to identify the presence of one or more particular microorganisms in a sample and/or to screen the microorganisms for drug susceptibility. The samples tested can be fluid or tissue samples from a patient (host) or may be environmental samples such as testing for food or water contaminations or swabs from surfaces to test for contaminations by infective organisms.

An exemplary product that could include the MID-AST device of the present disclosure is a bandage (e.g., a wound dressing) that has an embodiment of the MID-AST device integrated into the bandage to provide information about microorganism that may be present in the wound, for aiding in detecting infection and drug resistant infection, such as MRSA. In embodiments, the bandage can include a layered, absorbent pad having a surface layer adapted to contact a wound on a patient and allow the passage of fluids from the wound to layers adjacent to the surface layer, where the substrate of the device is contained in the absorbent pad of the bandage and in fluid communication with the wound. In such embodiments, the MID-AST device integrated into the bandage can include substrate layers of absorbent, flexible materials, such as the absorbent layers and propagation layers described above. The MID-AST device could include an upper layer of a gauze material to contact the wound surface, or in fluid communication with another part of the bandage that is in contact with the wound surface. In embodiments, the absorbent layer of the substrate can be a chromatographic paper to provide detection of viability and/or growth in the MID zones and AST region of the substrate, such that the device provides visible read-out to the wearer of the bandage. Various modifications and adaptations of the MID-AST device of the present disclosure are contemplated to accommodate a wide range of applications.

Methods of Making MID-AST Devices

The present disclosure also includes methods of making the MID-AST devices of the present disclosure described above. In embodiments, the method includes providing a substrate. The substrate may be made of any of the materials as described above. The method also includes modifying a surface of the substrate to provide spatially distinct identification zones in a microbe detection and identification (MID) region of the substrate and spatially distinct spots an antimicrobial susceptibility testing (AST) region of the substrate. The surface of the substrate can be modified in one or more of the ways described above. For instance a substrate may be modified with a support layer, a tie-layer, and/or micropatterning. The method may also include assembling one or more substrate layers, as well as micropatterning or otherwise modifying one or more layers as described above.

The method of making MID-AST devices of the present disclosure also includes patterning a growth medium composition on each MID zone, where the growth medium composition selects for one or more target microbial organisms and where. The growth medium composition can also include a matrix material as described above. The method can include spotting or otherwise applying the composition on the substrate. The composition can be spotted on the substrate by hand (e.g., manual pipetting) or automatically (e.g., a robotic arrayer). The growth medium composition can be the same or different for each identification zone (e.g., it may include a permissive medium for a permissive identification zone and a selective medium for a selective ID zone, as described above).

The method further includes patterning a growth medium/drug composition on each spot in an array in the AST region of the substrate. The growth medium/drug composition includes a growth medium and one or more antimicrobial drugs. In embodiments the growth medium/drug composition also includes a matrix material as described above. In embodiments the growth medium/drug composition for at least one spot includes a different drug, combination of drugs, or concentration of drugs that at least one other spot. Various combinations can be used, as described above, and the growth medium/drug composition can be applied/spotted onto the substrate as described above.

For some embodiments of methods of making MID-AST devices of the present disclosure, the method further includes placing the prepared substrate in a cassette as described above. Various modifications can be made to the methods of making the MID-AST devices of the present disclosure in order to accommodate modifications to the device as described above.

Microbial Identification and Antimicrobial Susceptibility Testing Systems

The present disclosure also provides MID-AST systems for high-throughput screening of test samples for a large number of microorganisms against a wide range of drugs. In embodiments, the MID-AST systems have removable chips/cassettes, where the chips can be disposable and different chips can be directed to screening different microorganisms. For instance, one chip can be directed to MRSA while another is directed to one or more *streptococcus* strains, and another can be directed to fungal organisms. Also, in the MID-AST devices of the present disclosure, in some embodiments, the MID zone and AST regions can be located on different chips as opposed to integrated onto a single chip/device.

Figure 4A:
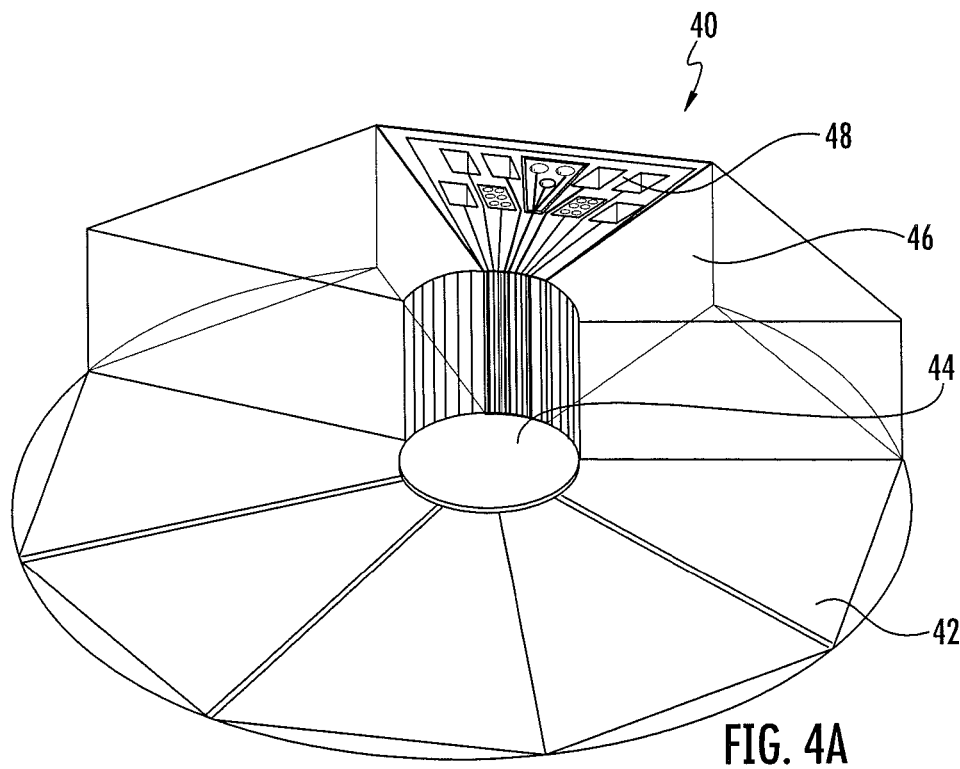
FIG. 4A illustrates an embodiment of a microbial identification and susceptibility testing system of the present disclosure, with FIG. 4B showing a close-up view of an embodiment of a cassette for use in an embodiment of the system illustrated in FIG. 4A.
Figure 4B:
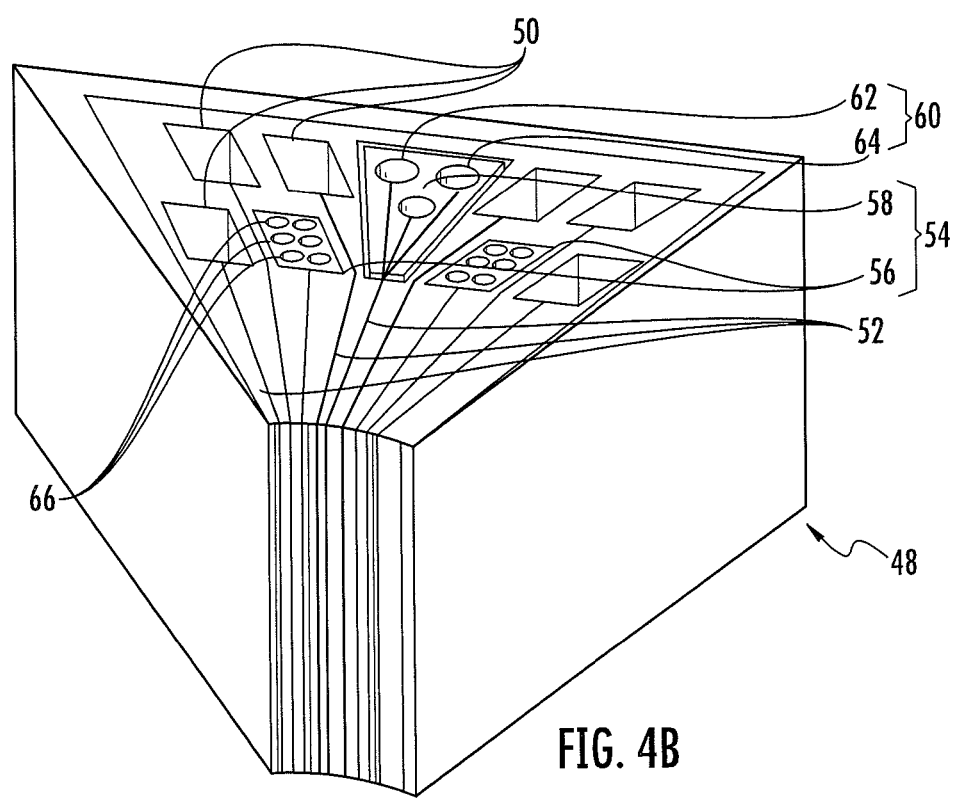

Various embodiments of the MID-AST system are contemplated, and general features are described here with reference to the embodiment illustrated in FIGS. 4A and 4B. Although the systems of the present disclosure are not limited to the specific configuration depicted in FIG. 4A and FB, the figures are illustrative of the relative orientation and features of the device.

Embodiments of the MID-AST systems (40) of the present disclosure include a housing (42), in embodiments the housing is a rotatable housing. The housing includes a sample inlet port (44), in embodiments it is a central sample inlet port, for receiving a test sample. The housing also includes a plurality of chambers (46) located around the sample inlet port, and each chamber is adapted for receiving a test cartridge (48). In embodiments, each chamber also includes an aperture providing fluid communication between the sample inlet port and a test cartridge housed within the chamber.

In embodiments, the MID-AST systems of the present disclosure also include one or more test cartridges (48) adapted for placement in a chamber (46) of the housing (42). In embodiments, the cartridges are removable. In embodiments, each test cartridge (48) includes a plurality of slots (50) and a plurality of channels (52) leading from the aperture of the chamber (46) to the slots (50) and providing fluid communication between the sample inlet port (44) and the slots (50), each slot (50) adapted for receiving a microbial test chip (54). In embodiments the microbial test chips (54) are adapted for placement in a slot (50) of a test cartridge (48). In embodiments, each test chip (54) is comparable to the MID-AST devices described above, except that in some embodiments the MID region and AST region are not both located on a single chip, but may be in different chips, such as illustrated by MID chip (58) and AST chip (56) in FIG. 4B. In embodiments each test chip (54) includes a flat substrate made of one or more layers as described above. In embodiments each test cartridge (48) includes at least one test chip that is a microbe detection and identification (MID) test chip and at least one test chip that is an AST chip. Details regarding the materials of the chips, layers, patterns, and test compounds are described in detail above with respect to the MID-AST devices of the present disclosure.

In embodiments, the MID-AST system of the present disclosure includes one or more spatially distinct microbial identification zones, e.g., an MID chip (58), and one or more microchannels adapted to conduct a portion of the test sample from the channels in the test cartridge (52) to the MID zones (60), each MID zone (60) including a medium that selects for growth of one or more target microbial organisms, where detection of growth in a MID zone indicates the presence of the one or more target microbial organisms associated with that zone. The MID zones may also include a matrix material as described above. In embodiments, the MID chip (58) includes a permissive MID zone (62) and one or more selective MID zones (64). The permissive and selective zones can be as described above.

In embodiments, the MID-AST system includes one ore more spatially distinct antimicrobial susceptibility test zones, e.g., an AST chip (56), and one or more microchannels adapted to conduct a portion of the test sample from the channels in the test cartridge (52) to the AST spots (66) in the AST chip (56). In embodiments, each AST spot includes a growth medium and one or more antimicrobial drugs, and may include a matrix material as described above. In embodiments, at least one AST spot includes a different drug, combination of drugs, or concentration of drugs than at least one other AST spot. In embodiments, an absence of growth or an amount of growth detected in each spot indicates the susceptibility of the one or more microbial organisms present in the sample to the one or more drugs on that spot. Detection methods and agents are as described above.

In embodiments of the MID-AST systems of the present disclosure, the test chips are removable and/or disposable. In embodiments, the microbial identification and susceptibility testing system also includes a device for rotating the rotatable housing at a sufficient speed to cause a test sample placed in the central sample inlet port to travel through the microchannels to the slots. In embodiments, the device for rotating is a centrifuge adapted to accommodate the rotatable housing. In embodiments the housing can be rotated at a speed of about 20 rpm to about 200 rpm to cause the test sample to travel through the microchannels to the chips in the slots. In embodiments the system also includes a detection/imaging system that detects and/or analyzes a detectable signal produced by a viability and/or growth detection agent on the chips. The viability and/or growth detection agent and methods of detecting and analyzing the signals produced by such agents are described above. Various other embodiments of MID-AST systems can be designed within the scope of the present disclosure.

Methods of Identifying Microbes and Antimicrobial Susceptibility Testing

The present disclosure also includes methods of identifying microbial organisms in a sample and methods of testing the susceptibility of one or more target microbial organisms in a test sample to various antimicrobial drugs. Various aspects of the methods of the present disclosure are described with reference to the devices and systems described above. Briefly, embodiments of a method of identifying microbes and conducting antimicrobial susceptibility testing according to the present disclosure includes providing a test sample and using the devices and systems described above to test for the presence of one or more target microbial organisms in a test sample and also testing the susceptibility of one or more target microbes to a one or more known antimicrobial drugs.

In an illustrative embodiment, a method of the present disclosure includes providing and contacting the test sample with a MID-AST device of the present disclosure, such that the test sample contacts each of the identification zones and AST spots of the device. The method then includes incubating the device for a period of time (e.g., times ranging from about 3 to about 24 hours as described above). After incubation, the method includes detecting the presence of one or more target microbial organisms in one or more identification zones, where detecting the presence of the target microbial organism in an identification zone indicates the presence of that microbial organism in the test sample. In embodiments, detecting the presence of the target microbial organism in an ID zone includes the use of a viability/growth detection agent as described above. The method also includes detecting the growth of a target microbial organism in one or more AST spot, where the amount of growth of the target microbial organism on a spot corresponds to the susceptibility of the target microbial organism to the one or more drugs contained on that spot. The amount of growth can be based on the strength of a detectable signal (e.g. fluorescence intensity, percent color change, etc., such as described above).

In some embodiments the incubating time is from about 6 to about 24 hours. In embodiments, detecting viability or growth includes contacting the device with a viability detection agent, a growth detection agent, or both, where the viability detection agent produces a detectable signal to indicate the presence or growth of a microbial organism. In embodiments, the detection agents are selected from, but not limited to, fluorescent molecules, colorimetric dyes, chromogenic dyes, conjugated antibodies against specific bacterial surface proteins, and other agents described in above.

It should be emphasized that the embodiments of the present disclosure, particularly, any "preferred" embodiments, are merely possible examples of the implementations, merely set forth for a clear understanding of the principles of the disclosure. Each embodiment described herein is understood to be embodiments of the disclosure that are applicable to all aspects of the invention(s). It is contemplated that any embodiment discussed herein can be implemented with respect to any method or composition of the disclosure, and vice versa. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1—High-Throughput Antimicrobial Susceptibility Chip

Introduction

The present example describes a microarray platform for high-throughput antimicrobial susceptibility testing (AST-Chip) to alleviate the issues with current AST technology, such as time and cost. As a proof of concept, the embodiment described in the present example is a chip-based platform for rapidly testing the antibiotic susceptibility of community-acquired *Staphylococcus aureus* (CA-MRSA) associated with skin and soft tissue infections (SSTIs); however, other embodiments of the AST-Chip can test for other bacterial and other microbial organisms, separately or on the same chip, or multiple chips in the same device.

CA-MRSA accounts for a vast majority of skin abscesses, has high rates of clinical failure and disease recurrence, puts close contacts and health care workers at risk of infection, is difficult to eradicate, and can cause fatal bacteremia. As compared to conventional methods for MRSA detection, the AST-Chip designed for the present example operates with a smaller sample volumes (30 nl), a shorter detection time (8-12 h), and improved or comparable sensitivity, is less expensive, and may be used on-site at a clinical microbiology lab with minimal training. Furthermore, the AST-Chip is culture independent, i.e., designed to work without the need to separately culture on selective growth plates.

Results and Discussion

Figure 5A:
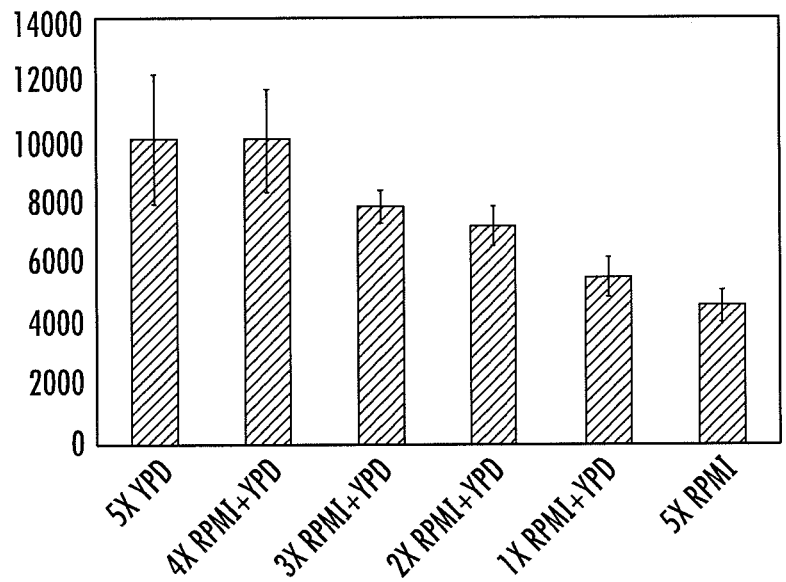
FIGS. 5A-5B illustrate optimization of growth conditions to favor S. aureus culture growth/biofilm formation in nanoscale.

A glass slide was selected as a substrate for the AST-Chip. A microscope glass slide was modified by printing nano-scale spots/islands of a hydrogel material containing antimicrobial agents in modified-growth medium for culture-independent screening. The clinical samples to be tested were subsequently printed and cultured on the islands. Susceptibility of microbial organisms in the test samples to the antimicrobial drugs contained in the spots was obtained from microbial cell density on each spot as measured by a fluorescence assay (FIG. 5).

The key steps in chip fabrication are described in below (these methods are also described in Srinivasan et al., which is incorporated by reference herein). The fabrication included three steps: (i) modification of the surface of glass slides with poly(styrene-co-maleic anhydride) (PSMA); (ii) printing spots of a 30 nl mixture of poly-l-lysine and barium chloride to create a "tie-layer" using a robotic microarrayer (Microsys, Digilab); and (iii) printing a 30 nl mixture of 0.5% alginate solution, optimized-growth medium and antimicrobial agents at various concentrations on top of the tie-layer. The gelation of alginate upon contact with the tie-layer provided and array of hydrophilic, drug-loaded islands on the hydrophobic background of the modified glass slide.

Figure 5B:
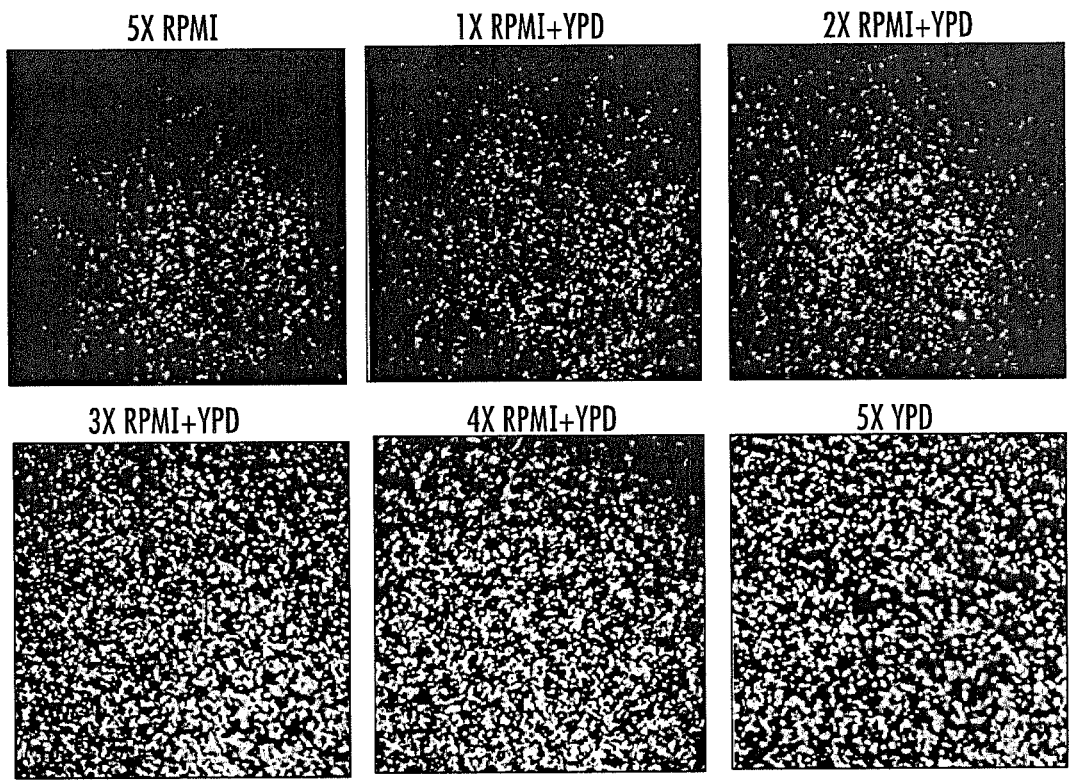

After printing, the AST-Chip had 1200 spots of gels loaded with different drugs at various concentrations; with each spot equivalent to a drug-loaded disc used in a disk diffusion assay. The spots had a volume of about 30 nl. The growth medium in the mixture was optimized by factorial design to promote the growth of Staphylococcus aureus (FIG. 5A) resulting in a concoction of 2× Yeast Peptone Dextrose (YPD), 3× Brain Heart Infusion (RPMI), and 10% human serum (FIG. 5B). Cells were observed to attach to the substrate in about 30 min, proliferated in 2-6 h, and were ready for assay in 8 h or less (FIG. 5B). In an embodiments, the cells were observed to mature into a biofilm with the production of exopolymeric matrix material in 6-10 h (data not shown). In comparison with the well-established in vitro macroscale models of bacterial biofilm formation in flasks and well plates, the nano-scale biofilms of the HT-AST Chip of the present example demonstrated morphological and architectural complexity of true biofilms despite 4000-fold miniaturization (FIG. 5B)

Figure 6A:
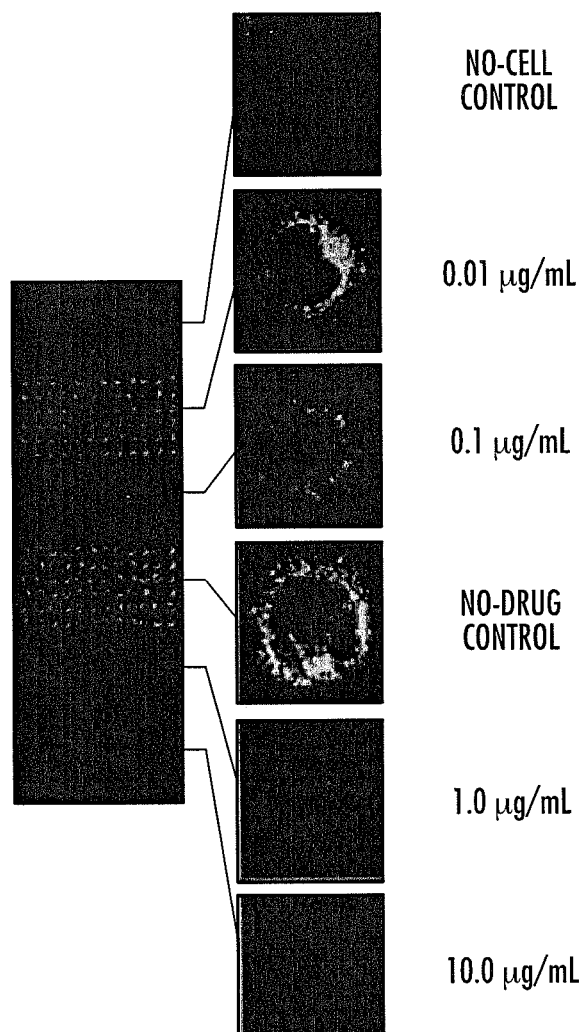
FIGS. 6A-6B illustrate antimicrobial susceptibility profile of methicillin against wild-type and methicillin-resistant Staphylococcus aureus as determined by devices of the present disclosure.
Figure 6B:
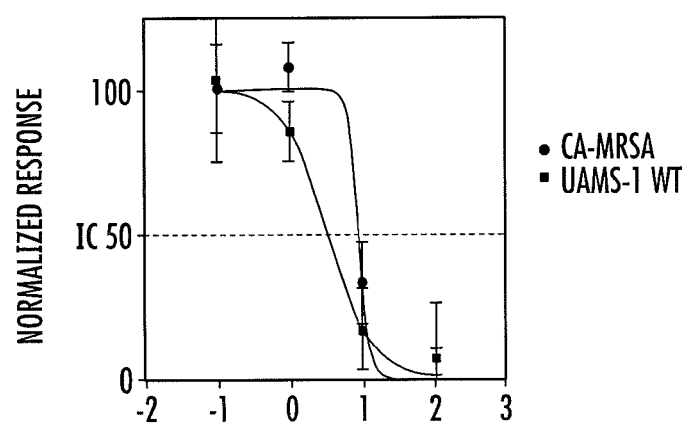

The AST-Chip was benchmarked by evaluating the antimicrobial-susceptibility of a wild type strain of Staphylococcus aureus (UAMS-1) and CA-MRSA (USA 300) against methicillin. The chip had 30 nl spots of 10, 1, 0.1, 0.01 µg/ml methicillin. 30 nl of bacterial cell suspension in alginate was printed on top of the methicillin spots, and the chip was incubated for 16 h to allow for drug action. A 16 h incubation period was used in order to simulate the conventional plate-based assays, but a shorter incubation time (3-12 h) can be used as well due to 1000-fold scale down in volume. After incubation, the cell density at different spots was quantified using FUN-1, a vital fluorescent dye with excitation and emission wavelength that is compatible with a standard microarray scanner and facilitating faster read out (FIG. 6A). The fluorescence intensity of control (no drug) and sodium hypochlorite-treated dead biofilms were set at 100% and 0%, respectively. The inhibitory effects of the antimicrobial agents were determined by the reduction in fluorescence intensity in comparison to the controls (FIG. 6B). The susceptibility profile obtained using the AST-Chip was comparable to the conventional/clinical methods of testing (Reller et al. 2009; Turnidge and Paterson 2007).

Figures 7A, 7B:
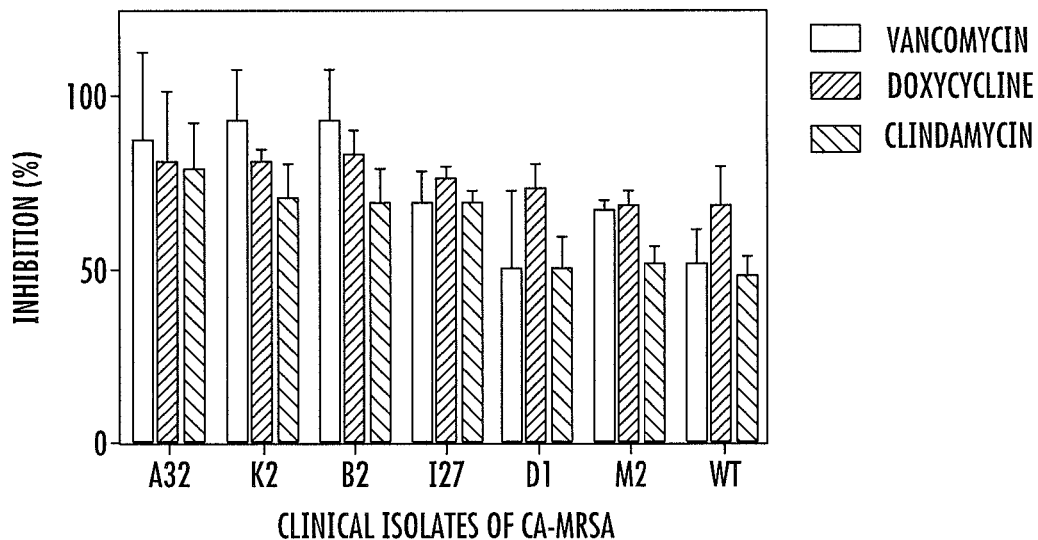
FIG. 7A is a bar graph illustrating the dose-response profile demonstrated by CA-MRSA isolates against doxycycline, clindamycin, and vancomycin in preventing the formation of CA-MRSA cultures/nano-biofilms on an embodiment of a MID-AST device of the present disclosure.
FIG. 7B is a table showing the data illustrated in the graph of FIG. 7A.

Next, an AST-Chip was designed and used to test the antibiotic-susceptibility of CA-MRSA clinical isolates collected from seven primary care practices affiliated with the South Texas Ambulatory Research Network (STARNet) Practice-Based Research Network (PBRN). The chip had spots with various combinations of 16 µg/ml of doxycycline, 4 µg/ml of clindamycin and 8 µg/ml of vancomycin with modified-media and alginate hydrogel. The spots were prepared and printed as described above. The clinical isolates and a wild type CA-MRSA strain were then printed on top of the chip, incubated for 16 h, and analyzed using FUN-1 as described above. FIG. 7A and Table 1 (FIG. 7B) show the inhibition of bacterial growth in the presence of antibiotics. While all the three drugs were shown to be effective against all seven isolates, it was observed that the relative effectiveness of the drugs against the isolates were significantly different: isolates A32, K2 and B2 were less susceptible to vancomycin than isolates I27, D1, M2 and WT. These results demonstrate that significant variations in susceptibility between different isolates exist, and that AST Chip can delineate these differences rapidly using small sample volumes.

This example describes a working embodiment of a rapid, robust, culture-independent, high density AST platform for CA-MRSA. Despite the nano-scale size for culturing bacteria, these results demonstrate phenotypic characteristics that are consistent with other established models. The technology is flexible and can be adapted to other bacterial and fungal organisms. In its current format, a single AST-Chip replaces up to twelve 96-well plates and several agar plates, which are used in broth dilution and disk diffusion assays, respectively. Thus by virtue of its miniaturization and automation, the use of this technology platform minimizes manual labor, cuts reagents use and drastically reduces assay costs.

Materials & Methods

Modification of Glass Substrates

Borosilicate glass slides were rinsed in a staining jar with 99% ethanol, and treated with concentrated sulphuric acid for 12 h. The slides were air-dried using a stream of nitrogen gas, rinsed with Milli-Q water and baked at 80° C. for 30 min. The slides were coated with 2.5% (wt/vol in toluene) 3-aminopropyltriethoxysilane (APTES) and baked at 120° C. for 15 min, generating a layer of cross-linked APTES. Finally, the slides were spin-coated with 0.3% (w/v in toluene) poly(styrene-co-maleic anhydride) (PSMA) at 3000 rpm for 30 s.

Printing of Antimicrobial Agents and S. aureus Cells

A solution of 0.01% poly-l-lysine and 100 mM Barium chloride ('tie-layer') was printed (30 nL per spot) on the functionalized PSMA-coated glass slides using a non-contact microarray spotter (Omnigrid Micro, Digilab Inc., Holliston, Mass.) with conically tapered 100 µm orifice ceramic tips. An array of 60 rows and 20 columns was printed at room temperature with relative humidity of 100%. In a standard print run, the tips were primed, rinsed in running water and vacuum dried twice after each sample-loading and printing step. Antimicrobial agents at defined concentrations in a modified microbial cell culture media was mixed with 0.5% alginate and 30 nL was spotted on top of the tie-layer.

The modified cell culture media in this case will be a combination of 2× Yeast Peptone Dextrose (YPD), 3× Brain Heart Infusion (RPMI), and 10% human serum.

After printing the drugs, $10^6$/ml of *Staphylococcus aureus* cell suspension in PBS or saline was printed (30 nL) on top of the drug spots. The slides were then placed in a humidified hybridization cassette (Arrayit, Calif.) to prevent evaporation of spots and incubated at 37° C. All microarrayer functions such as sample-loading, priming, printing and spatial distribution of the array were controlled by AxSys programming (Digilab). The chips may be incubated anywhere between 3-24 h to allow for the growth S. aureus in the presence of the drugs.

Viability Assay

The viability of the cells was determined based on their metabolic activity, using FUN 1 or BacLight. Upon staining, the fluorescent dye is internalized and processed only by metabolically active cells. The excitation and emission spectra of FUN 1 and BacLight are 480-535/550 nm and 488-500/690 nm respectively, are compatible with the sets of lasers and filters installed in most microarray scanners. The AST Chips were stained with 0.5 μM FUN 1 or 5 μM BacLight, by simply immersing the entire Chip in a staining jar, and incubated in the dark at 37° C. for 30 min. Following incubation, the Chip was washed three times by immersing in PBS to remove excess stain, air-dried, and scanned in a microarray scanner (GenePix Personal 4100A, Axon Instruments, Union City, Calif.). Images were analyzed with GenePix Pro V7 (Axon Instruments, Union City, Calif.).

Example 2—High-Throughput Microbial Identification and Antimicrobial Susceptibility Testing Device Introduction The present example describes a testing device, for rapid, simultaneous microbial identification and susceptibility testing. The microbial identification and susceptibility testing device can alleviate the current issues with conventional antimicrobial screening processes. This device integrates the identification of microbial pathogens and antimicrobial testing into a single unit. For the embodiment of the device described in the present example, the device is a paper-based microfluidic/microarray platform with defined zones for the identification of pathogen based on the selective culture and for the evaluation of antimicrobial susceptibility against a panel of antibiotics based on a colorimetric readout. The testing device works with small sample volume (e.g., 20 ul) and provides both pathogen ID and AST in about 3 to 6 hours (e.g., less than 4 h) with minimal sophistication for analysis, thus greatly accelerating and simplifying the current practice standards. An embodiment of such testing devise is illustrated in FIGS. 2A and 2B.

Optimization of Paper-Based Substrate

The microbial identification and susceptibility testing device for the present example employs a paper-based substrate for ease of use, cost effectiveness, and easy disposal. Thus, first a paper substrate was selected for properties such as absorbency and fluid conduction. To facilitate creation of isolated identification zones and susceptibility spots, micropatterning of hydrophobic borders/barriers and microchannels was tested and optimized, as illustrated in FIGS. 3A and 3B. Also, coatings of hydrophobic polymers were tested and optimized for imparting desired hydrophobicity to the paper (FIG. 3C). Finally, viability and growth detection compounds were tested to confirm the ability to detect viability and/or growth of cells in identification and susceptibility spots. In this embodiment, a colormetric dye, capable of indicating viability and distinguishing levels of growth, was chosen to provide for quick detection by visual inspection (FIGS. 3D and 3E, showing results with Presto blue viability indicator).

Device Design

The present example describes one embodiment of a microbial identification and susceptibility testing device of the present disclosure developed for detection and sensitivity analysis of *Staphylococcus aureus* and methicillin-resistant *S. aureus* (MRSA) from wound infections. While MRSA-associated infections are addressed first, as representing a major health concern, the platform can be expanded to other pathogens and infections. The present embodiment is a paper-based microarray/microfluidic Chip for selectively culturing *S. aureus* from a single or polymicrobial mixture or clinical sample in conjunction with antibiotic susceptibility tests (AST) of the mixture.

The designed test chip, illustrated in FIG. 2A, is 7 cm in length (a) and 2.5 cm in width (b) and includes three substrate layers (12) encased in a plastic cassette (20, 22) and covered with a transparent film (24) on top. In this embodiment, the substrate includes 3 layers: (i) a bottom solid substrate (18) made of silica or glass for support); (ii) a middle layer (16) of propagation pad made of micro-patterned hydrophobic nitrocellulose membrane to conduct the sample to hydrophilic absorbent pads; and (iii) a top layer (14) of absorbance pad made of micro-patterned chromatographic paper. As shown in FIG. 2B, the micropatterning allows for movement of cell samples and drug solutions through defined regions on paper substrates. On the top layer (14), a circular sample inlet (26) is patterned, followed by three square-shaped cell culture zones (30, 32, 34), making up a identification region (28), that eventually leads to a drug susceptibility zone (36) with individual drug loaded spots (38). The cell culture zones are, in series, blood agar (30) (for permissive growth), *S. aureus* isolation agar (32), and MRSA isolation agar (34) loaded with methicillin/nafcillin. The blood agar allows for the growth of all micro-organisms, the *S. aureus* isolation agar selects only for the growth of *S. aureus*, and methicillin/nafcillin/oxacillin-loaded isolation agar selects only for MRSA strains. The *S. aureus* isolation agar is Mannitol Salt agar with high concentration of sodium chloride that preferentially promotes the growth only of *S. aureus* from amongst the organisms commonly found in the wound samples. The drug susceptibility region (36) includes spots (38) of clinically used antibiotics over a range of concentrations and combinations dissolved in *S. aureus* isolation agar and printed on the nitrocellulose pad at 50 nL volume each with a microarray spotter (Microsys, Digilab, Mass.). All three layers units are housed in an air-tight plastic cassette lined with glycerol to maintain humidity and minimize drying. The top of the casing (22) contains windows for sample inlet and read-outs, sealed with a transparent film (24), which can be peeled off prior to use. The entire unit is assembled under sterile conditions and stored at 4° C. until use.

Upon use, the film is peeled off, the sample deposited onto the inlet (26) and then incubated at 22-37° C. with a relative humidity ranging from 25-75%. for approximately 3-6 hours. After incubation, the viability is qualitatively assessed in cell culture zones either from change in the color of phenol red in the cell culture zones and quantified in the susceptibility zone by PrestoBlue (Life Technologies) staining and image analysis (FIG. 2B)

REFERENCES

Dickert H, Machka K, Braveny I. 1981. The uses and limitations of disc diffusion in the antibiotic sensitivity testing of bacteria. Infection 9(1):18-24.
Institute CLS. 2013. Performance standards for antimicrobial susceptibility testing: Twenty-third informational supplement. M100:S23.
Jorgensen J H, J D. T. 2007. Antibacterial susceptibility tests: dilution and disk diffusion methods. Manual of clinical microbiology. American Society for Microbiology; (9th ed.):1152-72.
Mak A, Miller M A, Chong G, Y. M. 2009. Comparison of PCR and culture for screening of vancomycin-resistant enterococci: highly disparate results for vanA and vanB. J Clin Microbiol 47(12):4136-7.
Nightingale J. 1987. Clinical limitations of in vitro testing of microorganism susceptibility. Am J Hosp Pharm 44(1): 131-7.
O'Toole G, Kaplan H B, Kolter R. 2000. BIOFILM FORMATION AS MICROBIAL DEVELOPMENT. Annual Review of Microbiology 54(1):49-79.
Qaseem A, Alguire P, Dallas P, Feinberg L E, Fitzgerald F T, Horwitch C, Humphrey L, LeBlond R, Moyer D, Wiese J G and others. 2012. Appropriate use of screening and diagnostic tests to foster high-value, cost-conscious care. Ann Intern Med 156(2):147-9.
Reller L B, Weinstein M, Jorgensen J H, Ferraro M J. 2009. Antimicrobial Susceptibility Testing: A Review of General Principles and Contemporary Practices. Clinical Infectious Diseases 49(11):1749-1755.
Richter S S, M J. F. 2007. Susceptibility testing instrumentation and computerized expert systems for data analysis and interpretation. Manual of clinical microbiology. American Society for Microbiology: 245-56.
Srinivasan A, Leung K P, Lopez-Ribot J L, Ramasubramanian A K. 2013. High-throughput nano-biofilm microarray for antifungal drug discovery. mBio 4(4).
Turnidge J, Paterson D L. 2007. Setting and Revising Antibacterial Susceptibility Breakpoints. Clinical Microbiology Reviews 20(3):391-408.
Wanger A, Mills K, Nelson P W, Rex J H. 1995. Comparison of Etest and National Committee for Clinical Laboratory Standards broth macrodilution method for antifungal susceptibility testing: enhanced ability to detect amphotericin B-resistant *Candida* isolates. Antimicrob Agents Chemother 39(11):2520-2.
Wolk D M, Picton E, Johnson D, Davis T, Pancholi P, C C. G. 2009. Multicenter evaluation of the Cepheid Xpert methicillin-resistant *Staphylococcus aureus* (MRSA) test as a rapid screening method for detection of MRSA in nares. J Clin Microbiol 47(3):758-64.
Barenfanger J, Drake C, Kacich G. Clinical and financial benefits of rapid bacterial identification and antimicrobial susceptibility testing. J Clin Microbiol. 1999; 37(5):1415-18.
Performance standards for antimicrobial susceptibility testing: Twenty-third informational supplement. Clinical Laboratory Standards Institute 2013; M100:S23.

The invention claimed is:

1. A microbial identification and antimicrobial susceptibility testing (MID-AST) device comprising a flat, paper-based substrate having a microbial detection and identification (MID) region located in one area of the substrate and an antimicrobial susceptibility testing (AST) region located in another area of the substrate, the paper-based substrate comprising at least two interfacing layers:
   a propagation layer made of a hydrophobic paper material capable of conducting a fluid test sample to various regions of the substrate and comprising hydrophobic micropatterns on the hydrophobic paper material, the micropatterns defining microchannels and microborders, wherein the microchannels direct flow of the fluid test sample to the MID region and the AST region and wherein the microborders delineate one or more spatially distinct identification zones in the MID region and one or more borders of the AST region, wherein the microborders provide a hydrophobic barrier around each zone and region such that the zones and regions are spatially distinct and are capable of receiving and retaining a portion of the liquid test sample;
   an absorbent layer overlaying the propagation layer, the absorbent layer made of an absorbent paper material and comprising hydrophobic micropatterns corresponding to the micropatterns of the propagation layer, such that each layer has corresponding microchannels and microborders delineating the MID and AST regions and configured to receive and retain a portion of the liquid test sample within the corresponding microchannels and regions of the two interfacing layers, the absorbent layer further comprising:
      in the MID region, two or more spatially distinct identification zones, each identification zone comprising a self-contained island comprising a solgel or hydrogel matrix material and a growth medium that supports the growth of one or more target microbial organisms, the matrix material at least partially encapsulating the growth medium, wherein at least one identification zone is a permissive identification zone comprising a non-selective growth medium that allows non-selective growth of multiple genus and species of micro-organisms and wherein at least one other identification zone is a selective identification zone comprising a selective growth medium that selects for growth of only a specific genus or species of target microorganism, such that, after contact with the fluid test sample, detection of growth in an identification zone indicates that the test sample includes the one or more target microbial organisms selected for within that zone;
      in the AST region, at least one micropatterned array comprising a plurality of spatially distinct spots, each spot comprising a self-contained island comprising a solgel or hydrogel matrix material, a growth medium, and one or more antimicrobial drugs, wherein at least one spot comprises a different drug, combination of drugs, or concentration of drugs than at least one other spot, and wherein after contact with the fluid test sample, an absence of growth detected in each spot or reduced amount of growth detected in each spot, relative to a spot without the drug(s), indicates the susceptibility of the one or more microbial organisms present in the sample to the one or more drugs on that spot.

2. The MID-AST device of claim 1, wherein each identification zone and each spot further comprise a viability detection agent, a growth detection agent, or both, wherein the viability or growth detection agent produces a detectable signal indicating the growth or presence of viable microbial organisms on the zone or spot.

3. The MID-AST device of claim 1, wherein the one or more target microbial organisms is a gram positive or gram negative bacteria and wherein at least one antimicrobial drug in one or more spots in the antimicrobial susceptibility testing region is an antibiotic.

4. The MID-AST device of claim 1, wherein at least one target microbial organism is an antibiotic-resistant bacterium.

5. The MID-AST device of claim 1, wherein at least one target microbial organism is methicillin-resistant *S. aureus* (MRSA) and wherein the selective identification zone comprises an *S. aureus* selective identification zone comprising an *S. aureus* selection media and further comprising at least one other selective identification zone comprising a MRSA selective identification zone comprising a MRSA selection media comprising methicillin, nafcillin, vancomycin, or combinations thereof.

6. The MID-AST device of claim 1, wherein at least one target microbial organism is a fungus and wherein at least one antimicrobial drug in one or more spots in the antimicrobial susceptibility testing region is an antifungal drug.

7. The MID-AST device of claim 1, wherein the matrix material and growth medium combination for the identification zones and the matrix material, growth medium and drug combinations for the spots in the AST region are spotted on the absorbent layer with a microarray spotter.

8. The MID-AST device of claim 1, wherein the hydrophobic paper material of the propagation layer is selected from the group consisting of: filter paper, chromatographic paper, nitrocellulose membranes, cellulose-co-carbon fibers, cellulose-co-graphene, cellulose copolymers, and poly(3,4-ethylenedioxythiophene).

9. The MID-AST device of claim 1, wherein the absorbent paper material of the absorbent layer is selected from the group consisting of: chromatographic paper, gauze, filter papers, chromatographic papers, nitrocellulose membranes, cellulose-co-carbon fibers, cellulose-co-graphene, cellulose copolymer membranes, and other absorbent papers.

10. The MID-AST device of claim 1, wherein the hydrophobic micropatterns comprise a hydrophobic material selected from the group consisting of: paraffin, wax, transparent tape, poly-methyl-methacrylate, polystyrene, polyvinyl chloride, polydimethylsiloxane, co-polymers of styrene, olefins, acrylics, amides, imides, dienes, esters, ethers, and silicone.

11. The MID-AST device of claim 1, wherein the hydrophobic paper material of the propagation layer comprises hydrophobic nitrocellulose and wherein the absorbent paper of the absorbent layer comprises chromatographic paper.

12. The MID-AST device of claim 1, wherein the device further comprises a flat solid substrate under the paper substrate.

13. The MID-AST device of claim 12, wherein the solid substrate comprises a material selected from the group consisting of: glass, quartz, a metal substrate, a silicon substrate, a polymeric material and combinations thereof.

14. The MID-AST device of claim 1, wherein the device further comprises a cassette adapted to house the paper substrate, the cassette comprising a bottom tray and a top cover, wherein the top cover comprises an aperture for a sample inlet and windows for viewing the MID region and the AST region of the paper substrate.

15. The MID-AST device of claim 1, wherein the matrix material comprises a solgel, or a natural or synthetic hydrogel material selected from the group of solgels and hydrogels consisting of: a tetramethoxyorthosilicate, a methyltrimethoxyorthosilicate, a tetraalkoxyorthosilicate, a trialkoxyorthosilicate, a polyacrylamide, a polyacrylate, a sugar-substituted polyacrylate, polyethylene glycol (PEG), a polyvinyl alcohol, agarose, collagen, matrigel, alginate, chitosan, and other polysaccharide gels.

16. The MID-AST device of claim 1, wherein a group of spots in the AST region comprise the same antimicrobial drug, with each spot in the group comprising a different concentration of the drug and wherein analysis of the amount of growth detected in each spot of the group provides a minimum inhibitory concentration (MIC) value of the antimicrobial drug with respect to a target microbial organism.

17. The MID-AST device of claim 1, further comprising a layered absorbent pad having a surface layer adapted to contact a wound on a patient and allow the passage of fluids from the wound to layers adjacent to the surface layer, wherein the paper substrate of the MID-AST device is contained in the absorbent pad, wherein the absorbent pad comprising the MID-AST device is capable of serving as a MID-AST bandage in fluid communication with the wound.

18. A method of identifying and testing the susceptibility of one or more target microbial organisms in a test sample, the method comprising
providing a test sample and a MID-AST device according to claim 1;
contacting the test sample with the MID-AST device such that the test sample contacts each of the identification zones and spots of the device;
incubating the device for a period of time;
screening for the presence of a target microbial organism in one or more identification zones, wherein detecting the presence of the target microbial organism in an identification zone indicates the presence of that microbial organism in the test sample;
screening for growth of a target microbial organism in one or more antimicrobial susceptibility testing spots, wherein detection of growth and the amount of growth of the target microbial organism on a spot corresponds to the susceptibility of the target microbial organism to the one or more drugs contained on that spot.

19. The method of claim 18, wherein each identification zone and each spot of the MID-AST device further comprise a viability detection agent, a growth detection agent, or both contained within the self-contained islands of the MID and AST regions, such that, after the MID-AST device is contacted with the test sample and incubated, the viability or growth detection agent produces a detectible signal indicating the growth or presence of viable microbial organisms on the zone or spot, and wherein screening for the presence of a target microbial organism in one or more identification zones and one or more antimicrobial susceptibility testing zones includes detecting the signal produced by the viability or growth detection agent.

20. The MID-AST device of claim 2, wherein each identification zone comprises a chromogenic growth detection agent and each spot comprises a chromogenic viability detection agent, such that, after contact with a test sample, growth and viability can be visually assessed in each identification zone of the MID region and each spot of the AST region.

* * * * *